(12) United States Patent
Yamanaka et al.

(10) Patent No.: US 9,115,164 B2
(45) Date of Patent: Aug. 25, 2015

(54) SUBSTITUTED AROMATIC COMPOUND, HYDROGELATION AGENT, HYDROGEL, AND METHOD FOR GELATING AQUEOUS SAMPLE

(75) Inventors: Masamichi Yamanaka, Shizuoka (JP); Daisuke Higashi, Shizuaoka (JP)

(73) Assignees: NATIONAL UNIVERSITY CORPORATION SHIZUOKA UNIVERSITY, Shizuoka (JP); NISSAN CHEMICAL INDUSTRIES, LTD., Tokyo (JP)

( * ) Notice: Subject to any disclaimer, the term of this patent is extended or adjusted under 35 U.S.C. 154(b) by 171 days.

(21) Appl. No.: 14/003,907

(22) PCT Filed: Mar. 9, 2012

(86) PCT No.: PCT/JP2012/056185
§ 371 (c)(1),
(2), (4) Date: Sep. 9, 2013

(87) PCT Pub. No.: WO2012/121394
PCT Pub. Date: Sep. 13, 2012

(65) Prior Publication Data
US 2014/0005279 A1   Jan. 2, 2014

(30) Foreign Application Priority Data

Mar. 10, 2011   (JP) ................. 2011-053564

(51) Int. Cl.
| | | |
|---|---|---|
| *C07C 275/34* | (2006.01) |
| *C07C 275/28* | (2006.01) |
| *C07C 275/04* | (2006.01) |
| *C07H 15/08* | (2006.01) |
| *C07H 15/18* | (2006.01) |
| *C07H 15/203* | (2006.01) |
| *A23L 1/05* | (2006.01) |

(52) U.S. Cl.
CPC ............... *C07H 15/203* (2013.01); *A23L 1/05* (2013.01); *C07C 275/34* (2013.01); *C07H 15/18* (2013.01)

(58) Field of Classification Search
CPC .. C07C 275/04; C07C 275/28; C07C 275/34; C07H 15/08; C07H 15/18; C07H 15/203
See application file for complete search history.

(56) References Cited

FOREIGN PATENT DOCUMENTS

| | | |
|---|---|---|
| JP | 2003327949 A | 11/2003 |
| JP | 2005013174 A | 1/2005 |
| JP | 2005194257 A | 7/2005 |
| JP | 2007217551 A | 8/2007 |
| JP | 2008189559 A | 8/2008 |
| JP | 2009524819 A | 7/2009 |
| WO | WO-2010101147 A1 | 9/2010 |

OTHER PUBLICATIONS

International Search Report for PCT/JP2012/056185, dated Jun. 5, 2012.

*Primary Examiner* — Kendra D Carter
(74) *Attorney, Agent, or Firm* — Marshall, Gerstein & Borun LLP

(57) ABSTRACT

According to the present invention, a substituted aromatic compound represented by the following general formula (I) is provided. In general formula (I), $A^1$, $A^2$, and $A^3$ each independently represent an aryl group substituted by a hydrophilic group.

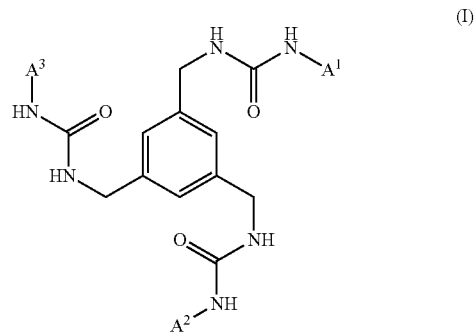

16 Claims, 3 Drawing Sheets

SUBSTITUTED AROMATIC COMPOUND, HYDROGELATION AGENT, HYDROGEL, AND METHOD FOR GELATING AQUEOUS SAMPLE

TECHNICAL FIELD

The present invention relates to a substituted aromatic compound, a hydrogelation agent, a hydrogel, and a method for gelating an aqueous sample.

BACKGROUND ART

Generally, gels are widely used in various fields such as the field of industry, the field of daily commodities, the field of the environment, the medical field, the field of cosmetics, the field of food, the field of agriculture, fields related to living organisms and the analytical field, by, for example, adding a gel to a paint, a resin or the like in the fields of paints or resins to adjust fluidity, or by gelating waste oil, waste liquid, waste water or the like to a solid material to prevent water pollution, or the like. "Gel" refers to a structure in which a fluid such as water and an organic solvent is contained in a three-dimensional mesh structure formed by a chemical substance. Here, when the fluid is an organic solvent, the gel is referred to as an organogel, and when the fluid is water, the gel is referred to as a hydrogel.

In recent years, application of a gel to a technique such as sensing and screening of a living organism-related sample or an environmental sample has been investigated. In this case, gelation in an aqueous environment, namely a hydrogel or a hydrogelation agent, needs further development.

As a technique related to a hydrogel or a hydrogelation agent, a hydrogelation agent consisting of a specific glycoside amino acid derivative (for example, see Japanese Patent Application Laid-Open (JP-A) Nos. 2003-327949 and 2005-13174), a hydrogel manufactured from a specific 2'-deoxyuridine derivative (for example, see JP-A No. 2005-194257) and a hydrogelation agent containing a specific benzamide derivative as an active ingredient (for example, see JP-A No. 2007-217551) are known.

As a compound expressing gelation activity with respect to an aqueous sample, a substituted aromatic compound of a specific structure having a hydrophilic portion located at the frame part of the molecule and a hydrophobic portion located at the central part of a molecule is known (for example, see the pamphlet of WO 2010/101147).

SUMMARY OF INVENTION

Technical Problem

The hydrogelation agents described in the above JP-A Nos. 2003-327949, 2005-13174 and 2007-217551 are compounds having a long-chain alkyl group and a structure having low molecular symmetry. In addition, the 2'-deoxyuridine derivative as described in the above JP-A No. 2005-194257 has no long-chain alkyl group, but still has a structure having low molecular symmetry. The reason that the conventional hydrogelation agents described above have a long-chain alkyl group and the reason that the conventional hydrogelation agents have a structure having low symmetry are not clear, but it is thought that the structure of these conventional hydrogelation agents is a structure that was discovered based on the empirical rules of gelation agents.

Namely, the conventional method for developing a hydrogelation agent is a method that relies on empirical rules in which a group consisting of many compounds (compound library) is construed, and a compound allowing gelation is discovered from the group, and there are not yet any definite established guidelines for the molecular design of the hydrogelation agent. In addition, the number of structures that can be selected for the long-chain alkyl group or the structure having low symmetry is enormous, and thus it is difficult to build a systematic compound library to begin with.

Regarding this point, the substituted aromatic compound described in the above pamphlet of WO 2010/101147 is a compound having a highly symmetric structure, which exhibits gelation activity (gelation performance) with respect to an aqueous sample, but requires further improvement in terms of gelation performance, and is needed to gelate an aqueous sample at a reduced addition amount.

In addition, a hydrogel prepared by a conventional hydrogelation agent may be problematic in terms of thermal stability or temporal stability.

Accordingly, an object of the present invention is to provide a substituted aromatic compound that has a non-conventional chemical structure, that has superior gelation performance with respect to an aqueous sample, and that can gelate an aqueous sample even at a reduced addition amount.

Further, an object of the present invention is to provide a hydrogelation agent including the substituted aromatic compound.

Further, an object of the present invention is to provide a hydrogel that includes the substituted aromatic compound, and has excellent thermal stability and temporal stability.

Further, an object of the present invention to provide a method of gelating an aqueous sample using the substituted aromatic compound, which allows easy gelation of an aqueous sample.

Solution to Problem

Means for solving the problems described above are as described below.

<1> A substituted aromatic compound represented by the following general formula (I):

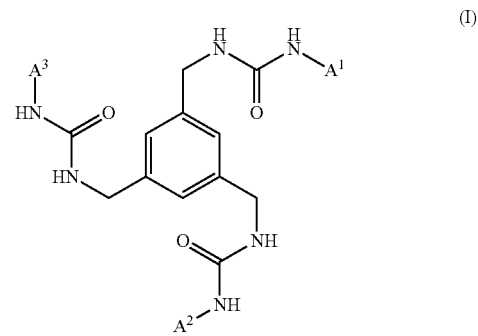

In general formula (I), $A^1$, $A^2$, and $A^3$ each independently represent an aryl group substituted by a hydrophilic group.

<2> The substituted aromatic compound as described in <1>, wherein the hydrophilic group comprises at least one selected from the group consisting of a —OH group, a —SO$_3$H group, a —SO$_3$M group, a —COOH group, a —COOM group, a —NR$^1$R$^2$R$^3$X group, a —NH$_2$ group, an alkyleneoxy group, and a saccharide group; M represents an alkali metal element; R$^1$, R$^2$, and R$^3$ each independently represent an alkyl group; and X represents a halogen element.

<3> The substituted aromatic compound as described in <1> or <2>, wherein the hydrophilic group is at least one selected from the group consisting of a —OH group, a —SO$_3$H group, a —SO$_3$M group, a —COOH group, a —COOM group, a —NR$^1$R$^2$R$^3$X group, a —NH$_2$ group, and a group including an alkyleneoxy group and a saccharide group; M represents an alkali metal element; R$^1$, R$^2$, and R$^3$ each independently represent an alkyl group; and X represents a halogen element.

<4> The substituted aromatic compound as described in any one of <1> to <3>, wherein the hydrophilic group is at least one selected from the group consisting of a —OH group, and a —[(OE)$_n$S$_g$] group; E represents an ethylene group; n represents an integer from 1 to 4; and S$_g$ represents a saccharide group.

<5> A hydrogelation agent, comprising the substituted aromatic compound as described in any one of <1> to <4>.

<6> A hydrogel comprising the substituted aromatic compound as described in any one of <1> to <4>.

<7> A method of gelating an aqueous sample, the method including contacting the substituted aromatic compound as described in any one of <1> to <4> with the aqueous sample.

Advantageous Effects of Invention

According to the present invention, it is possible to provide a substituted aromatic compound that has a non-conventional chemical structure, that has superior gelation performance with respect to an aqueous sample, and that can gelate an aqueous sample even at a reduced addition amount.

According to the present invention, it is possible to provide a hydrogelation agent including the substituted aromatic compound.

According to the present invention, it is possible to provide a hydrogel that contains the substituted aromatic compound, and has excellent thermal stability and temporal stability.

According to the present invention, it is possible to provide a method of gelating an aqueous sample using the substituted aromatic compound, which allows easy gelation of the aqueous sample.

DESCRIPTION OF EMBODIMENTS

<Substituted Aromatic Compound>

Figure 1:
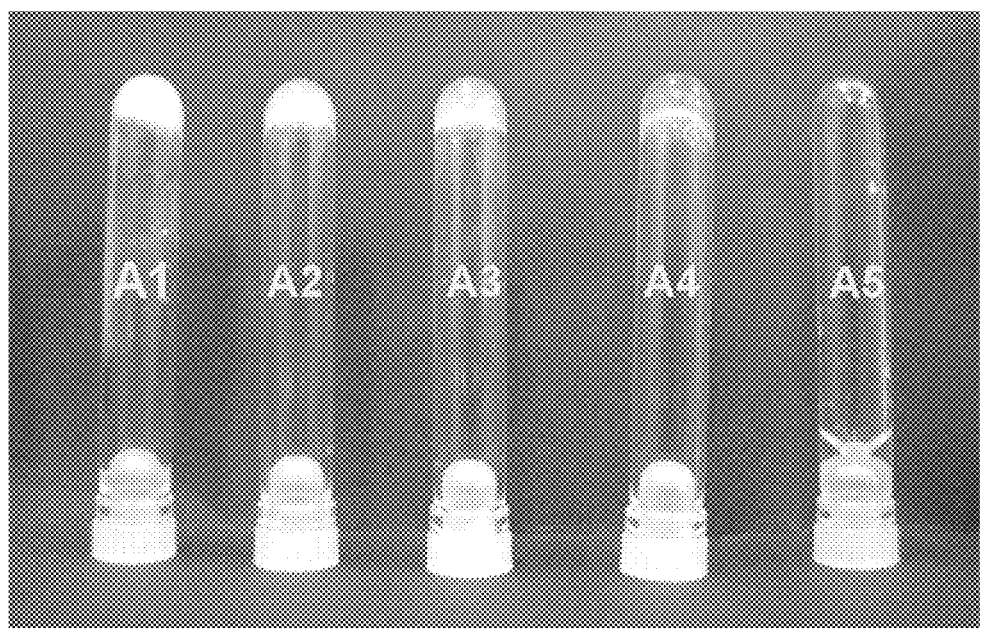
FIG. 1 is a photograph showing gelations of water were performed in Example 2.

The substituted aromatic compound of the present invention is a substituted aromatic compound represented by the following general formula (I) (hereinafter, also referred to as the "compound represented by general formula (I)").

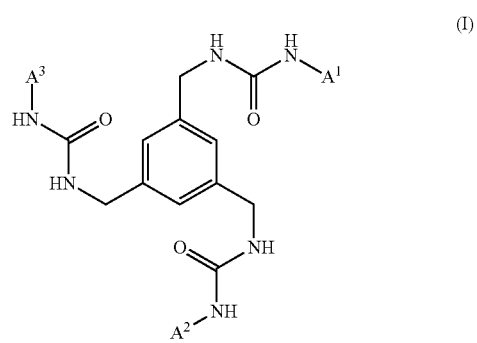

In general formula (I), A$^1$, A$^2$, and A$^3$ each independently represent an aryl group substituted by a hydrophilic group.

The compound represented by general formula (I) is a planar molecule consisting of a hydrophilic portion located at the frame part of the compound (specifically, a hydrophilic group substituted at the aryl group) and a hydrophobic portion located at the central part of the compound (the portion other than the hydrophilic portion).

The hydrophobic portion is of a highly symmetric structure including three urea structures.

The compound represented by general formula (I) allow easy gelation of an aqueous sample in which water is used as a solvent. Namely, the compound represented by general formula (I) is useful as a hydrogelation agent having excellent gelation performance with respect to an aqueous sample.

Hereinafter, the presumed gelation mechanism for gelation of an aqueous sample by the compound represented by general formula (I) is explained. However, the present invention is not limited to the gelation mechanism described below.

When the compound represented by general formula (I) (hereinafter, simply also referred to as the "molecule") is contacted with water, the molecules are self-assembled and overlap with each other, with the hydrogen bond between the urea parts and the interaction between the hydrophobic portions as major driving forces, whereby they are one-dimensionally assembled. As a result, a supermolecular assembly in fibrous form is formed, in which the molecules are one-dimensionally assembled. At this time, it is thought that π electrons present at the aryl group in A$^1$, A$^2$, and A$^3$ in one molecule interact with π electrons present at the aryl group in A$^1$, A$^2$, and A$^3$ in other molecules (π stacking), thereby further strengthening the bond between the molecules (overlapping).

The thus-formed supermolecular assemblies in fibrous form are assembled in the aqueous sample, to form a three-dimensional mesh structure. The supermolecular assemblies that have formed the three-dimensional mesh structure are not precipitated in the aqueous sample since they have affinity with water due to the hydrophilic portion included in each of the molecules.

Accordingly, it is thought that water is present in the gap portion of the formed three-dimensional mesh structure, whereby the fluidity of the aqueous sample decreases and gelation occurs.

The compound represented by general formula (I) has a highly symmetric structure, and thus is also excellent in view of easiness of synthesis and easiness of identification of the compound.

Furthermore, the compound represented by general formula (I) of the present invention has higher gelation performance than the substituted aromatic compound described in the pamphlet of WO 2010/101147.

Accordingly, the compound represented by general formula (I) can gelate an aqueous sample at a reduced addition amount than the substituted aromatic compound described in the pamphlet. Furthermore, the compound represented by general formula (I) can gelate a broader kind of aqueous samples than the substituted aromatic compound described in the pamphlet.

A reason presumed for this is that the compound represented by general formula (I) of the present invention has a structure in which the benzene ring in the center portion of the molecule is linked to the three-urea structure with a methylene group (—$CH_2$— group), whereby to decrease the size of the hydrophobic portion in comparison to the substituted aromatic compound described in the pamphlet, and decrease the hydrophobicity (namely, increase the hydrophilicity) as a whole of the molecule.

Furthermore, the compound represented by general formula (I) of the present invention can decrease the molecular weight than the substituted aromatic compound described in the pamphlet, and thus is advantageous in view of easy synthesizability.

The "aqueous sample" in the present invention is not particularly limited if it is a sample comprising at least water as a solvent. The compound represented by general formula (I) of the present invention can gelate a broad range of aqueous samples as described above. For example, the compound represented by general formula (I) of the present invention can gelate an aqueous sample in a broad range of pH (for example, pH 1 to 12).

Examples of the aqueous sample include water, a buffer, a medium, and an inorganic aqueous solution (acidic aqueous solution, basic aqueous solution, neutral aqueous solution or the like).

Examples of the buffer include various buffers such as a sodium triphosphate (sodium phosphate) buffer, a Tris-hydrochloric acid (Tris-HCl) buffer, a 4-(2-hydroxyethyl)-1-piperazine ethane sulfonic acid-sodium hydroxide (HEPES-NaOH) buffer, a sodium acetate (NaOAc) buffer, a borate (Borate) buffer, a borate-sodium hydroxide (Borate NaOH) buffer, a Tris-glycine-sodium dodecyl sulfate (Tris-glycine-SDS) buffer, a Tris-borate-ethylene diamine tetraacetic acid (Tris-Borate-EDTA) buffer, a phosphate buffered saline (PBS) buffer, a glycine-sodium hydroxide (Glycine-NaOH) buffer, a glycine-hydrochloric acid (Glycine-HCl) buffer, a phosphate (Phosphate) buffer, and a sodium dihydrogen phosphate-sodium hydroxide ($NaH_2PO_4$—NaOH) buffer.

Examples of the medium include various mediums such as Dulbecco's Modified Eagle's Medium (D-MEM), Roswell Park Memorial Institute 1640 medium (RPMI1640 medium) and Ham F12 medium (F12 medium).

Examples of the inorganic aqueous solution include an aqueous solution of an acid such as hydrochloric acid, an aqueous solution of an alkali such as sodium hydroxide, and an aqueous solution of an inorganic salt such as a sodium salt and an ammonium salt (examples thereof including sea water and saline).

Confirmation of the gelation in the present invention is visually performed.

Specifically, 0.1 to 5 mL of an aqueous sample is put into a test tube having 5 to 20 mm of the inner diameter (hereinafter, also referred to as the "microtube"), and the test tube is turned upside down (such that the bottom of the test tube is up, and the opening of the test tube is down), and is allowed to stay still for 60 seconds.

A case where the sample did not flow downward after a lapse of 60 seconds is determined as being gelated.

The minimum concentration of the compound represented by general formula (I) in an aqueous sample that can gelate the aqueous sample is referred to as the "minimum concentration for gelation" in the present invention.

A low minimum concentration for gelation means that the compound represented by general formula (I) has excellent gelation performance, and can gelate the aqueous sample at a lower addition amount.

$A^1$, $A^2$, and $A^3$ in general formula (I) each independently represent an aryl group substituted by a hydrophilic group.

$A^1$, $A^2$, and $A^3$ may be the same group, or may be a different group, but are preferably the same group from a viewpoint of the symmetry of the compound represented by general formula (I).

In $A^1$, $A^2$, and $A^3$, the number of the hydrophilic groups with respect to the aryl group may be suitably adjusted depending on the demanded degree of hydrophilicity, but is preferably 1 to 3, more preferably 1 or 2 from a viewpoint of easy synthesizability and the like.

In $A^1$, $A^2$, and $A^3$, the substitution site of the hydrophilic group with respect to the aryl group is preferably the outermost location of the compound represented by general formula (I) from a viewpoint of the gelation activity.

Specifically, in the case where the aryl group is a phenyl group substituted by one hydrophilic group, the hydrophilic group is preferably substituted at the 4-position of the phenyl group. In the case where the aryl group is a phenyl group substituted by two hydrophilic groups, the hydrophilic groups are preferably substituted at the 3-position and the 5-position of the phenyl group. In the case where the aryl group is a phenyl group substituted by three hydrophilic groups, the hydrophilic groups are preferably substituted at the 3-position, the 4-position, and the 5-position of the phenyl group.

In general formula (I), examples of the aryl group in $A^1$, $A^2$, and $A^3$ include a phenyl group, a naphthyl group, and a biphenyl group. However, the aryl group is preferably a phenyl group from a viewpoint of allowing the compound represented by general formula (I) to have a low molecular weight, and the like.

The hydrophilic group in $A^1$, $A^2$, and $A^3$ is not particularly limited, but is preferably a group including at least one selected from a —OH group, a —$SO_3H$ group, a —$SO_3M$ group (M represents an alkali metal element), a —COOH group, a —COOM group (M represents an alkali metal element), a —$NR^1R^2R^3X$ group ($R^1$, $R^2$, and $R^3$ each independently represent an alkyl group, and X represents a halogen element), a —$NH_2$ group, an alkyleneoxy group, and a saccharide group.

Herein, the saccharide group represents a monovalent group derived from a sugar.

Specifically, the saccharide group refers to a residue obtained by removal of a hydrogen atom from one of the hydroxyl groups of a sugar.

The saccharide group may be substituted by a substituent such as an alkyl group (a methyl group, an ethyl group or the like) and a sulfo group.

The kind of the sugar is not particularly limited, but is preferably a monosaccharide or oligosaccharide from a viewpoint of the gelation activity, more preferably a monosaccharide or disaccharide, and particularly a preferably monosaccharide.

The monosaccharide is preferably a pentose or a hexose.

Examples of the pentose include ribose, deoxyribose, and fructose.

Examples of the hexose include glucose, mannose, galactose, methyl-α-glucose, and methyl-α-mannose.

Among those described above, the monosaccharide is preferably a hexose, and particularly preferably glucose, mannose, galactose, methyl-α-glucose or methyl-α-mannose.

Examples of the disaccharide include, for example, maltose, isomaltose, lactose, trehalose, sucrose, and cellobiose.

Among those described above, the disaccharide is particularly preferably maltose.

The alkyleneoxy group is preferably a $C_{1-10}$ alkyleneoxy group, more preferably a $C_{1-4}$ alkyleneoxy group, and particularly preferably an ethyleneoxy group (namely, a $C_2$ alkyleneoxy group) from a viewpoint of maintenance of the hydrophilicity.

The alkyleneoxy group is preferably bonded to the aryl group at the side of the oxygen atom. One alkyleneoxy group (hereinafter, also referred to as the "-AO— group") may be contained alone in one hydrophilic group, or two or more alkyleneoxy groups may be contained in the form that they are linked in a chain to have a structure of -(AO)$_n$— (n is, for example, an integer from 1 to 10).

The alkyl group represented by $R^1$, $R^2$, and $R^3$ is preferably a $C_{1-10}$ alkyl group, and more preferably a $C_{1-4}$ alkyl group from a viewpoint of maintenance of the hydrophilicity.

The alkali metal represented by M is preferably K or Na.

The halogen element represented by X is preferably F, Cl, Br, or I.

Among those described above, the hydrophilic group in $A^1$, $A^2$, and $A^3$ is preferably a group including at least one selected from a —OH group, a —SO$_3$H group, a —SO$_3$M group (M represents an alkali metal element), a —COOH group, a —COOM group (M represents an alkali metal element), a —NR$^1$R$^2$R$^3$X group ($R^1$, $R^2$, and $R^3$ each independently represent an alkyl group, and X represents a halogen element), a —NH$_2$ group, and a saccharide group (preferably, monosaccharide-derived saccharide group) and an alkyleneoxy group (preferably a $C_{1-4}$ alkyleneoxy group, more preferably an ethyleneoxy group) from a viewpoint of the gelation activity.

Furthermore, the hydrophilic group in $A^1$, $A^2$, and $A^3$ is more preferably at least one selected from a —OH group, a —SO$_3$H group, a —SO$_3$M group (M represents an alkali metal element), a —COOH group, a —COOM group (M represents an alkali metal element), a —NR$^1$R$^2$R$^3$X group ($R^1$, $R^2$, and $R^3$ each independently represent an alkyl group, and X represents a halogen element), a —NH$_2$ group, and a —[(OE)$_n$S$_g$] group (E represents an ethylene group, n represents an integer from 1 to 10 (preferably an integer from 1 to 4), and S$_g$ represents a saccharide group.), and particularly preferably a —OH group, or a —[(OE)$_n$S$_g$] group (herein, E represents an ethylene group, n represents an integer from 1 to 4 (preferably an integer from 1 to 3) and S$_g$ represents a saccharide group (preferably, a monosaccharide-derived saccharide group)).

Among these, the hydrophilic group is preferably a —OH group from a viewpoint of the easily synthesizability. The hydrophilic group is preferably a —[(OE)$_n$S$_g$] group from a viewpoint of the gelation performance.

The compound represented by general formula (I) is preferably a low molecular weight compound, specifically, a compound having a molecular weight of 3000 or less, more preferably a compound having a molecular weight of 1500 or less from the viewpoint of the easy synthesizability and the like. The lower limit of the molecular weight of the compound represented by general formula (I) is preferably 500 from the viewpoint of the gelation activity and the like.

More specifically, the molecular weight of the compound represented by general formula (I) is preferably 500 to 3000, and more preferably 500 to 1500 from the viewpoint of the gelation activity and the synthesizability and the like.

The compound represented by general formula (I) can be synthesized by, for example, the method described below.

First, 1,3,5-Tris(amino methyl)benzene (the compound (7) described below) is reacted with an aromatic compound having a hydrophilic group (for example, a —OH group, a —[(OE)$_n$S$_g$] group, or the like) protected with a protective group, and an isocyanate group (—NCO group). Herein, as the protective group, a general protective group for a hydrophilic group (an acetyl group, a t-butyldimethyl silyl group, a methoxymethyl group, a benzyl group, or the like) may be used.

Then, the amino group of the terminal of 1,3,5-Tris(amino methyl)benzene reacts with the isocyanate group (—NCO group) of the aromatic compound whereby to produce a precursor compound (for example, the compound (13), the compound (16) and the like described below) of the structure where the hydrophilic group of the compound represented by general formula (I) is protected with a protective group.

Next, the obtained precursor compound is deprotected to obtain the compound represented by general formula (I).

As a method for the deprotection, a known method may be used, for example, a treatment with an acid, a treatment with a base, a treatment with a fluoride ion, or a treatment with catalytic hydrogenation.

In the synthesis method described above, the hydrophilic group may be suitably selected from the hydrophilic groups described above in consideration of a balance of the hydrophilicity and the hydrophobicity of the molecule as a whole.

As described with the example of the synthesis method described above, the compound represented by general formula (I) of the present invention can be easily synthesized based on the theoretical molecular design to introduce a hydrophilic group into the outside of the highly symmetric hydrophobic portion in consideration of a balance of the hydrophilicity and the hydrophobicity.

Preferable examples of the aryl group that is substituted by the hydrophilic group and is represented by $A^1$, $A^2$, and $A^3$ include the groups represented by the formulae (a-1) to (a-55) described below. However, $A^1$, $A^2$, and $A^3$ in the present invention are not limited to the groups described below.

In formulae (a-1) to (a-55) described below, "*" represents the bonding site of general formula (I) to the structure of urea.

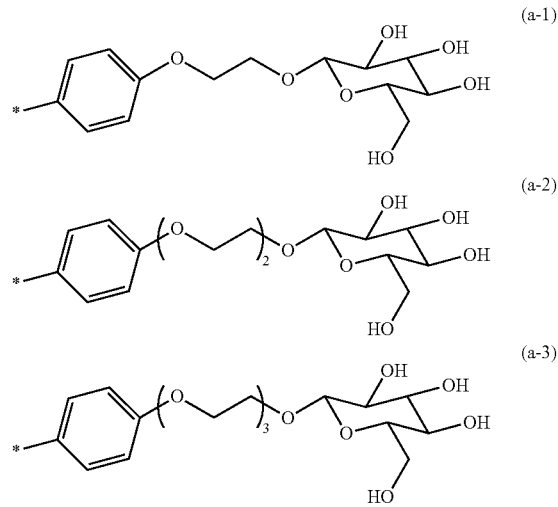

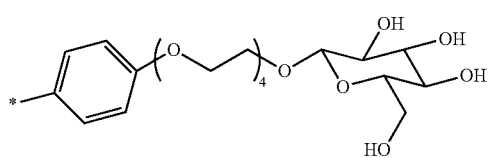
(a-4)
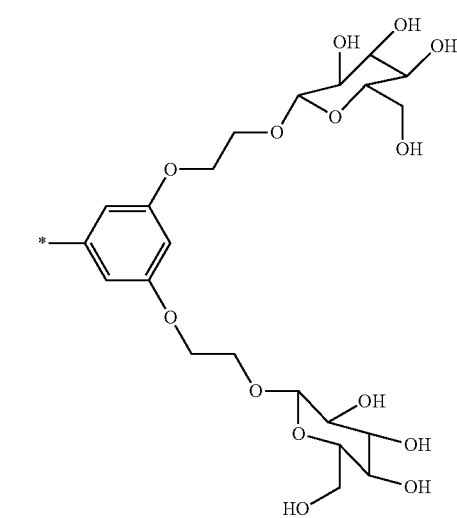
(a-5)
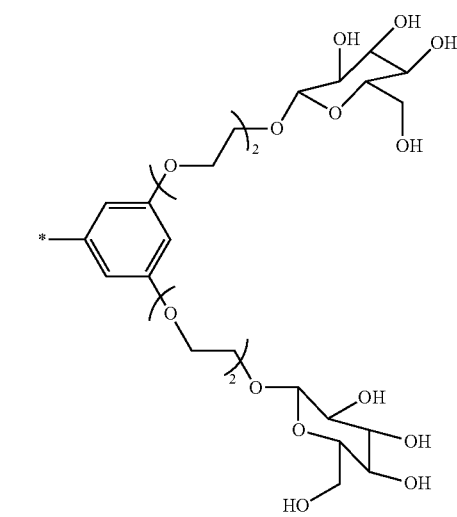
(a-6)
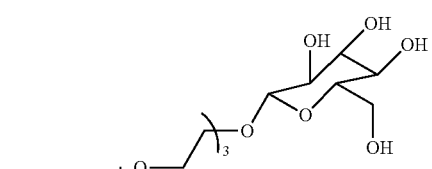
(a-7)
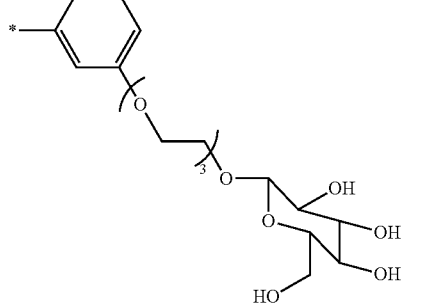
(a-8)
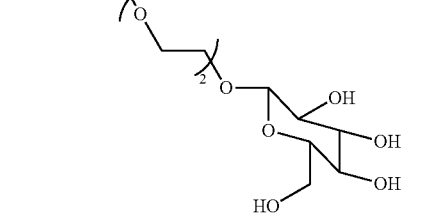
(a-9)

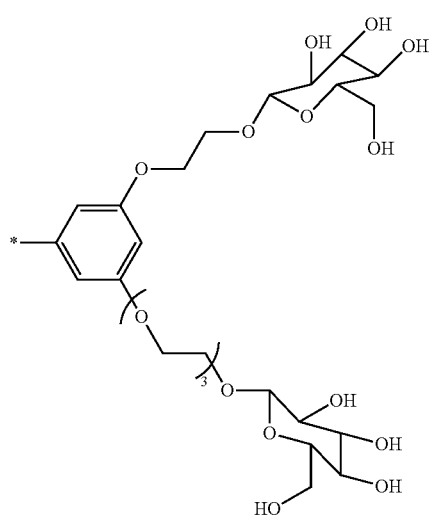
(a-10)
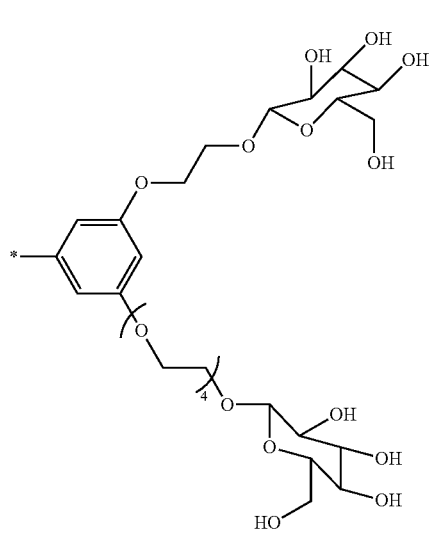
(a-11)
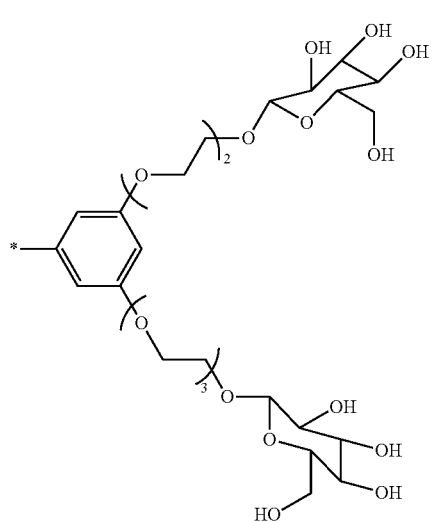
(a-12)
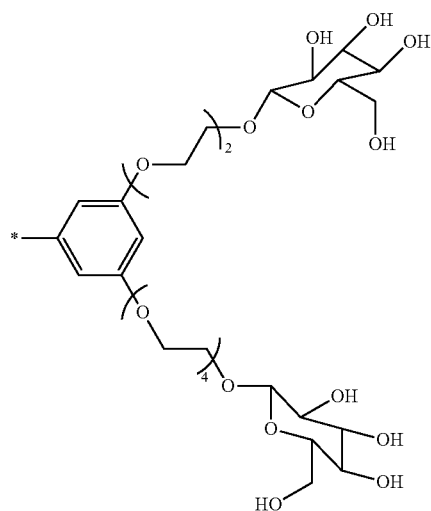
(a-13)
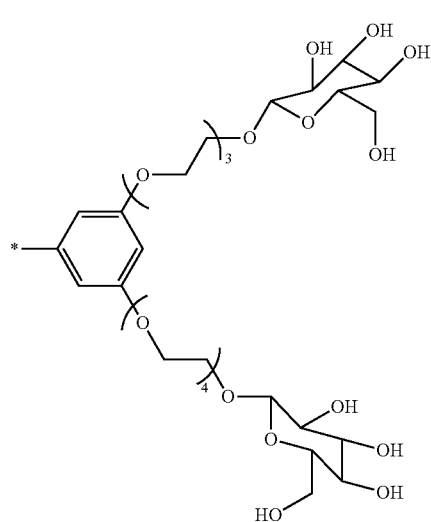
(a-14)
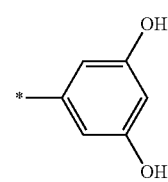
(a-15)
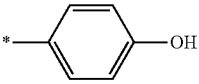
(a-16)
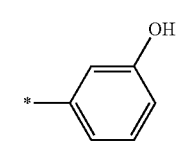
(a-17)
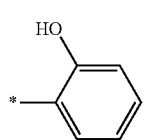
(a-18)

-continued
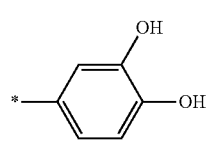 (a-19)
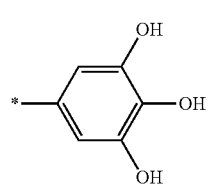 (a-20)
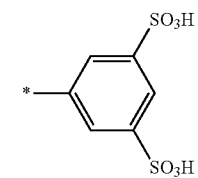 (a-21)
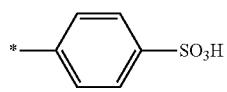 (a-22)
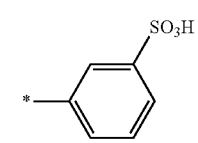 (a-23)
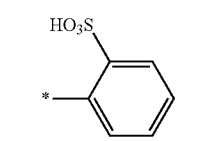 (a-24)
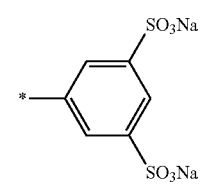 (a-25)
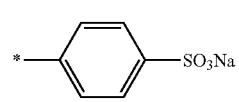 (a-26)
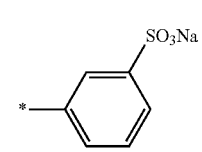 (a-27)
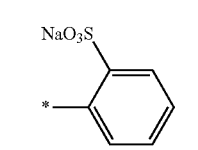 (a-28)
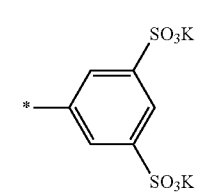 (a-29)
-continued
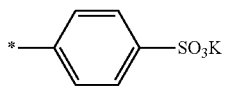 (a-30)
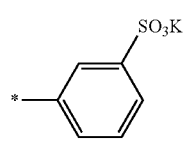 (a-31)
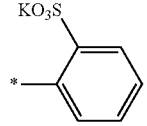 (a-32)
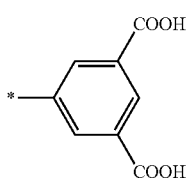 (a-33)
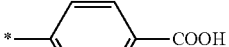 (a-34)
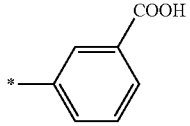 (a-35)
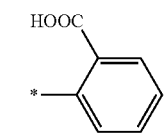 (a-36)
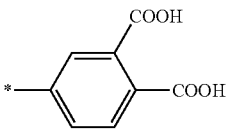 (a-37)
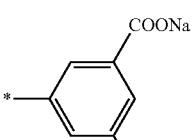 (a-38)
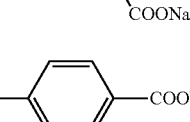 (a-39)
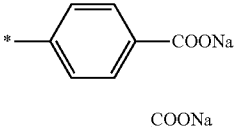 (a-40)

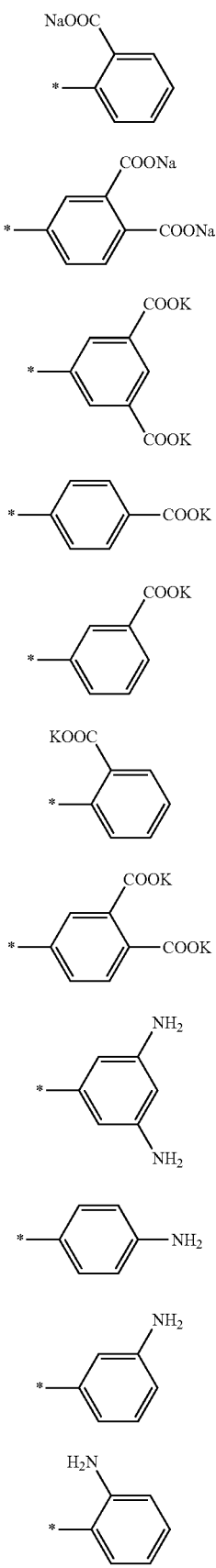

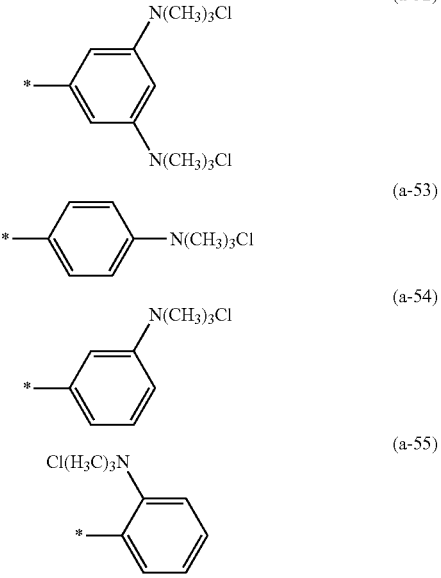

Next, specific examples of the compound represented by general formula (I) (exemplary compound) of the present invention are described.

The symbols such as (a-1) in the exemplary compounds described below represent the groups exemplified as preferable examples of $A^1$, $A^2$, and $A^3$ in the above.

However, the present invention is not limited to the exemplary compounds described below, and, of course, the scope of the invention includes, in addition to the exemplary compounds described below, compounds in which aryl groups each substituted by a hydrophilic group are suitably combined as $A^1$, $A^2$, and $A^3$.

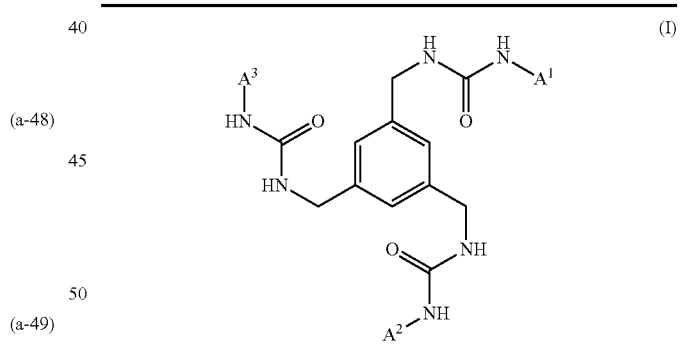

| Exemplary Compound | $A^1$ | $A^2$ | $A^3$ |
|---|---|---|---|
| (I-1) | (a-1) | (a-1) | (a-1) |
| (I-2) | (a-2) | (a-2) | (a-2) |
| (I-3) | (a-4) | (a-4) | (a-4) |
| (I-4) | (a-5) | (a-5) | (a-5) |
| (I-5) | (a-6) | (a-6) | (a-6) |
| (I-6) | (a-8) | (a-8) | (a-8) |
| (I-7) | (a-9) | (a-9) | (a-9) |
| (I-8) | (a-11) | (a-11) | (a-11) |
| (I-9) | (a-2) | (a-2) | (a-1) |
| (I-10) | (a-2) | (a-1) | (a-1) |
| (I-11) | (a-2) | (a-2) | (a-6) |
| (I-12) | (a-2) | (a-6) | (a-6) |
| (I-13) | (a-2) | (a-2) | (a-15) |
| (I-14) | (a-2) | (a-15) | (a-15) |

-continued (I)

| Exemplary Compound | A¹ | A² | A³ |
|---|---|---|---|
| (I-15) | (a-2) | (a-2) | (a-21) |
| (I-16) | (a-2) | (a-21) | (a-25) |
| (I-17) | (a-2) | (a-2) | (a-33) |
| (I-18) | (a-2) | (a-33) | (a-38) |
| (I-19) | (a-2) | (a-2) | (a-48) |
| (I-20) | (a-2) | (a-48) | (a-52) |

(I)

| Exemplary Compound | A¹ | A² | A³ |
|---|---|---|---|
| (I-21) | (a-15) | (a-15) | (a-15) |
| (I-22) | (a-16) | (a-16) | (a-16) |
| (I-23) | (a-20) | (a-20) | (a-20) |
| (I-24) | (a-21) | (a-21) | (a-21) |
| (I-25) | (a-22) | (a-22) | (a-22) |
| (I-26) | (a-25) | (a-25) | (a-25) |
| (I-27) | (a-26) | (a-26) | (a-26) |
| (I-28) | (a-33) | (a-33) | (a-33) |
| (I-29) | (a-34) | (a-34) | (a-34) |
| (I-30) | (a-38) | (a-38) | (a-38) |
| (I-31) | (a-39) | (a-39) | (a-39) |
| (I-32) | (a-43) | (a-43) | (a-43) |
| (I-33) | (a-44) | (a-44) | (a-44) |
| (I-34) | (a-48) | (a-48) | (a-48) |
| (I-35) | (a-49) | (a-49) | (a-49) |
| (I-36) | (a-52) | (a-52) | (a-52) |
| (I-37) | (a-53) | (a-53) | (a-53) |
| (I-38) | (a-15) | (a-15) | (a-16) |
| (I-39) | (a-15) | (a-20) | (a-20) |
| (I-40) | (a-15) | (a-15) | (a-33) |
| (I-41) | (a-15) | (a-15) | (a-26) |
| (I-42) | (a-15) | (a-15) | (a-38) |
| (I-43) | (a-15) | (a-15) | (a-48) |
| (I-44) | (a-15) | (a-15) | (a-49) |

<Hydrogelation Agent>

The hydrogelation agent of the present invention the compound represented by general formula (I) described above.

Namely, the form of the hydrogelation agent of the present invention may be a form in which the hydrogelation agent consists of the compound represented by general formula (I) described above, or may be a form of a combination of the compound represented by general formula (I) described above and other ingredients (the form of a combination may be a mixture form, or not a mixture form).

In the case where the hydrogelation agent in the non-mixture form is added to water, the compound represented by general formula (I) and the other ingredients may be added at the same time, or may be added separately.

Examples of the other ingredients include a binder ingredient, and a solute of a buffer.

<Hydrogel>

The hydrogel of the present invention includes the compound represented by general formula (I) described above.

This hydrogel has excellent thermal stability, and also has excellent temporal stability (for example, under the atmosphere or in water), since the hydrogel includes the compound represented by general formula (I) described above that has superior gelation performance with respect to an aqueous sample.

A hydrogel prepared with a conventional hydrogelation agent may have problems in the thermal stability or the temporal stability. Particularly, a heat-soluble hydrogel prepared with a conventional low molecular weight gelation agent may have problems in the thermal stability.

For example, the thermal stability at 40° C. to 50° C. may be demanded in cosmetics, quasi-pharmaceutical products, pharmaceutical preparations, inks/paints/coating materials (for stationery, for print, for construction) and the like using a hydrogel. In addition, the equatorial or new equatorial regions or desert regions are also assumed as the situation where the hydrogel is used. Even the region other than the equatorial or near-equatorial regions or the desert regions (for example, in Japan), for example, the temperature inside of an automobile in the summer, and the like may be elevated to 60° C. or higher. Under such high temperature environment, a hydrogel prepared with a conventional hydrogelation agent often fails to maintain the gel state.

Contrary to the conventional hydrogel, the hydrogel of the present invention has high thermal stability (for example, maintaining the gel state when heated to 90° C.), and thus can be used in various kinds of situation.

Examples of a specific form of the hydrogel of the present invention include a form in which at least water (and, if necessary, other ingredients) is present in the gap portion of the three-dimensional mesh structure formed by self-assembly of the compounds represented by general formula (I).

Herein, the three-dimensional mesh structure is, as described above, a structure formed by further assembling of supermolecular assemblies in the fibrous form formed by self-assembly of molecules of the compound represented by general formula (I) to each other.

The content of the compound represented by general formula (I) in the hydrogel of the present invention is not particularly limited if the content is an amount that is equal to or more than the amount corresponding to the minimum concentration for gelation.

The hydrogel of the present invention is preferably prepared by, for example, the method of gelating an aqueous sample described below.

Hereinafter, the gelation reaction of the aqueous sample is also referred to as the "phase transfer reaction from sol to gel".

By using this phase transfer reaction from sol to gel, it is possible to perform the screening, that is, selection of the target compound having a specific property (property to strongly interact with a specific compound) from a group of unknown test compounds.

The hydrogel of the present invention is in the gel state at room temperature (15° C. to 25° C.) similarly to a general hydrogel, but when external stimulation (stimulation by heating, physical stimulation such as stirring, addition of a chemical substance, or the like) is applied to the hydrogel of the present invention, the self-assembly of molecules of the compound represented by general formula (I) to each other is solved and solation occurs.

One example of the solation of the hydrogel by addition of a chemical substance is a reaction of solation by dissolution the self-assembly of molecules of the compound represented by general formula (I) to each other by addition of an anion. The anion may be added in a form such as a metal salt, for example, a sodium salt.

The anion added herein is preferably an anion that interacts with the urea part of the compound represented by general formula (I) from a viewpoint of effectively dissolving the self-assembly of molecules of the compound represented by general formula (I) to each other. Specific examples of such anion include halogen ions such as fluorine ion ($F^-$), chlorine ion ($Cl^-$), bromine ion ($Br^-$) and iodine ion ($I^-$), acetic acid ion ($CH_3COO^-$), and the like.

Another example of solation of the hydrogel by addition of a chemical substance is a reaction of solation by dissolving the self-assembly of molecules of the compounds represented by general formula (I) to each other by adding lectin which strongly interacts with a hydrophilic group (a saccharide group) of the terminal of the compound represented by general formula (I).

Hereinafter, the solation reaction of the hydrogel is also referred to as the "phase transfer reaction from gel to sol".

The hydrogel of the present invention may be also used as a gel for electrophoresis, when containing sodium dodecyl sulfate (SDS) as necessary.

Namely, a target substance (protein, nucleic acid and the like) can be developed on the hydrogel of the present invention by electrophoresis. In this case, the target substance can be effectively collected by solating the hydrogel in which the target substance is developed, from gel to sol by the phase transfer reaction.

For example, when the hydrogel of the present invention is used as a gel for protein electrophoresis, it is possible to collect a protein sample in an amount capable of analysis such as MALDI/TOFMS (matrix assisted laser deionization/time-of-flight mass spectrometer) from the spots after the electrophoresis.

<Method of Gelating Aqueous Sample>

The method of gelating an aqueous sample of the present invention includes contacting the compound represented by general formula (I) described above with an aqueous sample.

The contact can be performed by adding and mixing the compound represented by general formula (I) with the aqueous sample.

After the mixing, the mixture may be left for 1 hour or more as necessary, whereby to gelate the aqueous sample.

In the method of gelating an aqueous sample of the present invention, at least one of heating treatment and ultrasonic treatment may be conducted for the aqueous sample after the contact with the compound represented by general formula (I) as necessary in order to enhance the gelation activity.

Herein, the heating treatment and the ultrasonic treatment may be used in combination.

As a method in which the heating treatment and the ultrasonic treatment are combined, the heating treatment and the ultrasonic treatment may be performed sequentially (any of the treatments may be performed first), or the heating treatment and the ultrasonic treatment may be performed at the same time.

The heating treatment is performed at the condition of, for example, 70° C. or higher (preferably 80° C. or higher).

The heating time is, for example, 30 minutes or more (preferably 60 minutes or more).

After the heating treatment, the mixture may be cooled to, for example, room temperature (15° C. to 25° C.), which allows further progress of the gelation.

The ultrasonic treatment is performed, for example, using a commercially available ultrasonic treatment device for 5 minutes or more (preferably for 15 minutes or more).

Although the heating treatment and the ultrasonic treatment are explained above, these treatments are not necessary in the method of gelating an aqueous sample of the present invention. From a viewpoint of suppressing denaturation of a living organism-related sample including protein, sugar and the like, it is preferable that the heating treatment or the ultrasonic treatment is not performed.

The substituted aromatic compound, the hydrogelation agent, and the method of gelating an aqueous sample of the present invention enables excellent gelation activity with respect to an aqueous sample, and the hydrogel of the present invention has high thermal stability and excellent temporal stability. Therefore, the substituted aromatic compound, the hydrogelation agent, the hydrogel, and the method of gelating an aqueous sample of the present invention can be used in the medical field, the field of cosmetics, the field of food, the field of daily goods, the field of industry, the field of agriculture, the field of environment, the field related to a living organism and the analytical field, and the like.

Examples of specific use include SDS buffer gel for electrophoresis, hydrogel for cell incubation, water-quality examination and urine analysis.

Furthermore, the substituted aromatic compound, the hydrogelation agent, the hydrogel, and the method of gelating an aqueous sample of the present invention may be used in the screening described in the paragraphs 0075 to 0085 and 0167 to 0179 of the pamphlet of WO 2010/101147, or titration of the anion amount in an aqueous sample described in the paragraphs 0184 to 0188 of the pamphlet.

EXAMPLES

Hereinafter, Examples of the present invention are explained, but the present invention is not limited to these Examples. Meanwhile, "%" and "% by weight" in the Examples section represent "% by mass" unless stated otherwise. The "room temperature" in the Examples section represents 15° C. to 25° C.

Example 1

As Example 1, synthesis of an exemplary compound of the substituted aromatic compound of the present invention was performed.

<Synthesis of Exemplary Compound (I-2)>

The exemplary compound (I-2) was synthesized according to the synthesis route described below.

In the synthesis route described below, Me represents a methyl group, Ac represents an acetyl group, and Ts represents a tosyl group.

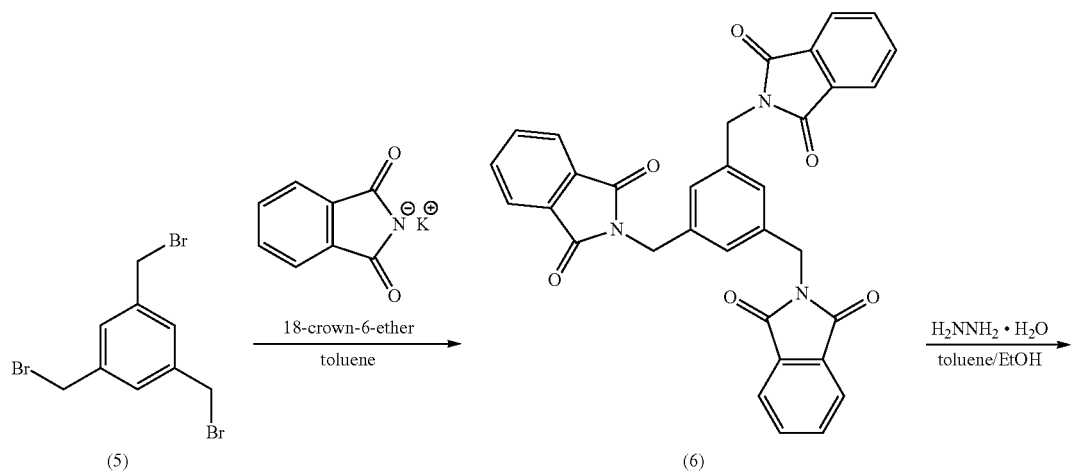
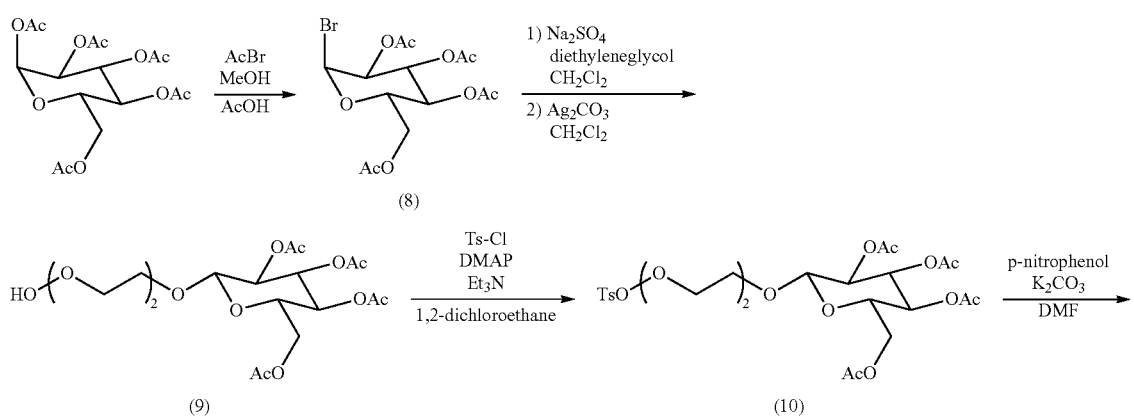
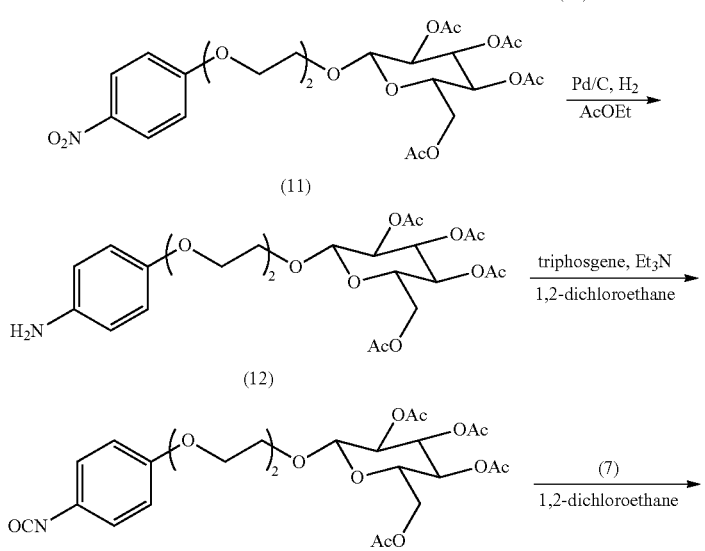

-continued
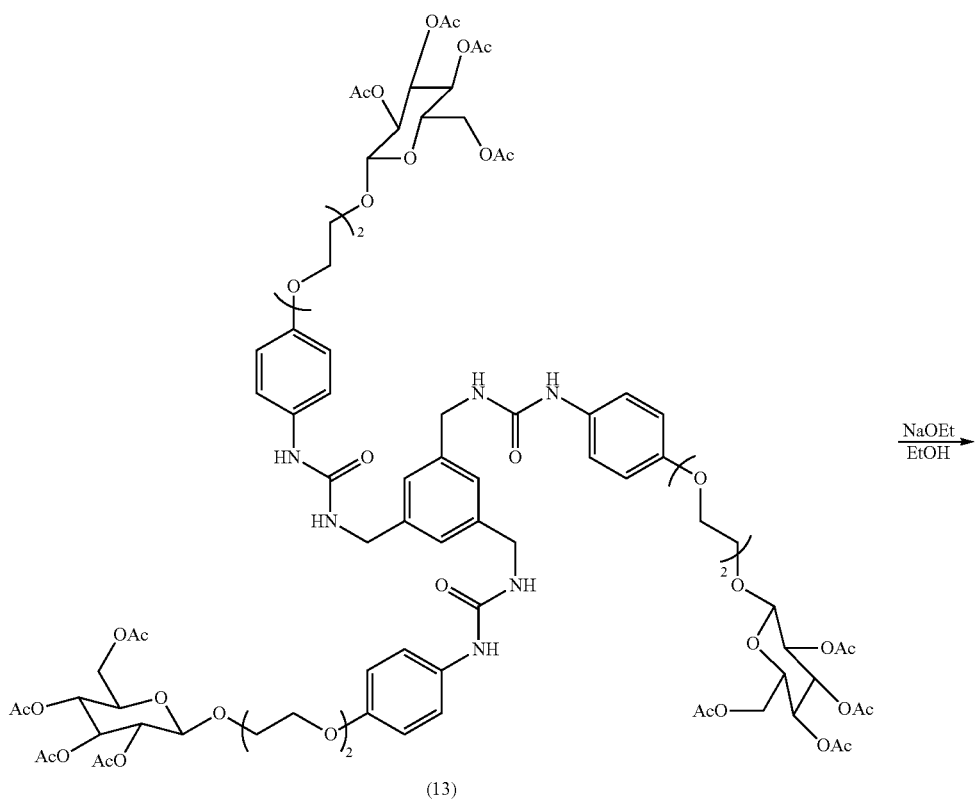
(13)
NaOEt
EtOH
→
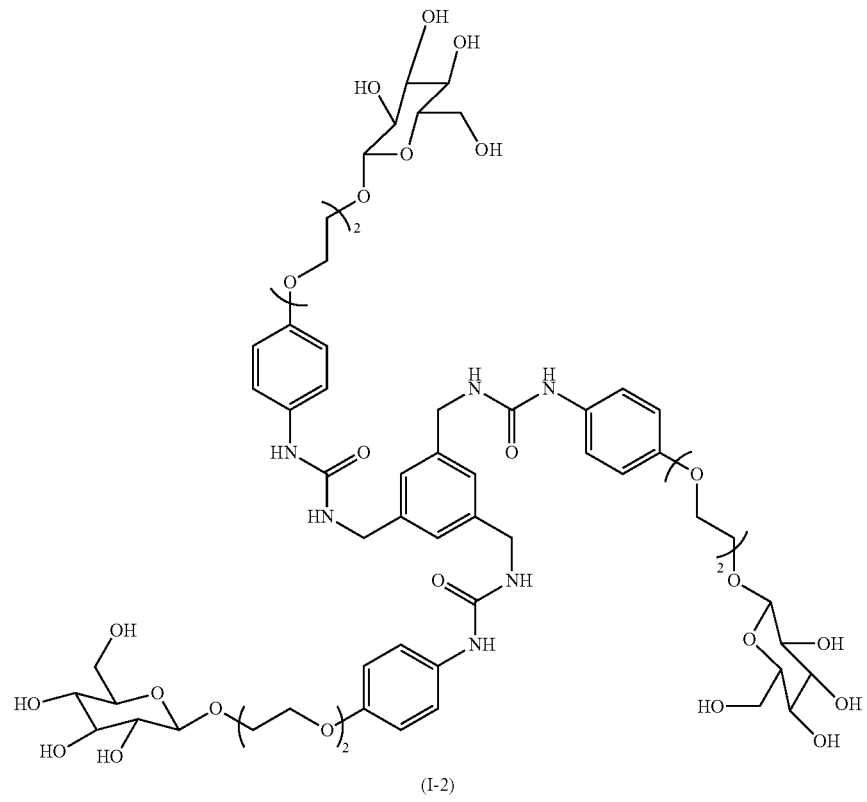
(I-2)

Hereinafter, specific manipulations of the synthesis route are described.

—Synthesis of Compound (6)—

The compound (5) (1,3,5-Tris(bromomethyl)benzene) (302 mg, 0.85 mmol), potassium phthalimide (562 mg, 3.03 mmol) and 18-crown-6-ether (67 mg, 0.25 mmol) were sequentially added under argon atmosphere, and then toluene (7.1 mL) was added. The obtained solution was refluxed for 27 hours. To the solution after the reflux, $CH_2Cl_2$ was added to dissolve the solid, and the organic layer was washed with $H_2O$ and the obtained organic layer was further washed with saturated saline. The solution after the washing was dried with addition of $Na_2SO_4$, subjected to natural filtration, and further concentrated, and purified with silica gel column chromatography (acetone/$CH_2Cl_2$=1:60). The obtained solid was subjected to methanol (MeOH)/ethyl acetate (AcOEt) reprecipitation to give the targeted compound, that is, the compound (6) as a white solid (79% yield rate, 369 mg yield amount).

The NMR measurement result of the compound (6) was as described below.

$^1$H NMR (400 MHz, $CDCl_3$) δ4.78 (s, 6H), 7.35 (s, 3H), 7.69-7.83 (m, 12H).

—Synthesis of Compound (7)—

To the compound (6) (1.00 g, 1.80 mmol), ethanol (EtOH) (24 mL) and toluene (12 mL) were added under argon atmosphere.

To the obtained solution, $H_2NNH_2 \cdot H_2O$ (0.52 mL, 10.8 mmol) was dropped under ice cooling, and the mixture was stirred at 72° C. for 17 hours. The solvent was distilled off under reduced pressure from the solution after the stirring, and then an aqueous solution of 40% potassium hydroxide (4.0 mL) was added to dissolve the solid, and extraction with $CHCl_3$ was performed. The organic layer was dried with addition of $Na_2SO_4$, subjected to natural filtration, and further concentrated, to give the unpurified targeted compound (the compound (7)) as an ocher solid (60% crude yield rate, 178 mg crude yield amount). Since the impurities could be removed in the next step, purification was not further performed herein.

The NMR measurement result of the compound (7) was as described below.

$^1$H NMR (400 MHz, $CD_3OD$) δ3.85 (s, 6H), 7.24 (s, 3H).

—Synthesis of Compound (8)—

To α,D-glucopyranose pentaacetate (1.00 g, 2.57 mmol), acetic acid (AcOH) (9.2 mL) was added under argon atmosphere. To the obtained solution, acetyl bromide (AcBr) (0.57 mL, 7.69 mmol) and methanol (MeOH) (0.15 mL, 3.70 mmol) were added, and the reaction solution was stirred at room temperature for one day under light-shielded conditions. The reaction solution after the stirring was concentrated, to give the unpurified targeted compound (the compound (8)) as a brown syrup-like liquid. Since the impurities can be removed in the next step, purification was not further performed herein.

The NMR measurement result of the compound (8) was as described below.

$^1$H NMR (400 MHz, $CDCl_3$) δ2.03 (s, 3H), 2.05 (s, 3H), 2.10 (s, 3H), 2.10 (s, 3H), 4.13 (dd, $J_1$=2.0 Hz, $J_2$=14.4 Hz, 1H), 4.29 (dd, $J_1$=6.3 Hz, $J_2$=5.4 Hz, $J_3$=1.5 Hz, 1H), 4.33 (dd, $J_1$=11.5 Hz, $J_2$=3.9 Hz, 1H), 4.83 (dd, $J_1$=10.0 Hz, $J_2$=3.9 Hz, 1H), 5.18 (t, J=9.8 Hz, 1H), 5.56 (t, J=9.8 Hz, 1H), 6.61 (d, J=3.9 Hz, 1H).

—Synthesis of Compound (9)—

To the unpurified compound (8), $CH_2Cl_2$ (107 mL) was added under argon atmosphere. To this, $Na_2SO_4$ (3.64 g, 25.6 mmol) and diethylene glycol (2.4 mL, 25.6 mmol) were added, and the mixture was stirred at room temperature for 15 minutes, and then $Ag_2CO_3$ (1.47 g, 5.35 mmol) was added thereto, and the resulting mixture was further stirred at room temperature for 19 hours. $Ag_2CO_3$ was removed with suction filtration from the obtained solution, and the solution was washed with water. The generated organic layer was washed with saturated saline, and then dried with $Na_2SO_4$. The obtained reaction mixture was purified with silica gel column chromatography (ethyl acetate/hexane=1:3→1:0), to give the targeted compound, that is, the compound (9) as a white solid (48% two-step yield rate, 535 mg yield amount).

The NMR measurement result of the compound (9) was as described below.

$^1$H NMR (400 MHz, $CDCl_3$) δ2.01 (s, 3H), 2.03 (s, 3H), 2.06 (s, 3H), 2.09 (s, 3H), 2.17-2.25 (m, 1H), 3.54-3.62 (m, 2H), 3.66 (t, J=4.6 Hz), 3.69-3.77 (m, 4H), 3.96 (dt, $J_d$=10.7 Hz, $J_t$=4.2 Hz, 1H), 4.15 (dd, $J_1$=12.7 Hz, $J_2$=2.5 Hz, 1H), 4.26 (dd, $J_1$=12.4 Hz, $J_2$=4.9 Hz, 1H), 4.61 (d, J=7.8 Hz, 1H), 5.00 (dd, $J_1$=9.5 Hz, $J_2$=7.8 Hz, 1H), 5.10 (t, J=9.8 Hz, 1H), 5.21 (t, J=9.5 Hz, 1H).

—Synthesis of Compound (10)—

To paratoluene sulfonyl chloride (tosyl chloride; Ts-Cl) (258 mg, 1.35 mmol) and N,N-dimethyl-4-amino pyridine (DMAP) (4.9 mg, 0.040 mmol), 1,2-dichloroethane (2.8 mL) was added under argon atmosphere. To this, the compound (9) (536 mg, 1.23 mmol) and triethyl amine ($Et_3N$) (0.55 mL, 3.96 mmol) were added, and the resulting mixture was stirred at room temperature for 20 hours.

The solution after the stirring was quenched with a saturated aqueous solution of sodium hydrogen carbonate, and then and extracted with $CH_2Cl_2$. The generated organic layer was washed with saturated saline, and dried with $Na_2SO_4$. The obtained reaction mixture was purified with silica gel column chromatography (ethyl acetate/hexane=1:1→1:0), to give the targeted compound, that is, the compound (10) as a colorless transparent syrup-like liquid (81% yield rate, 587 mg yield amount).

The NMR measurement result of the compound (10) was as described below.

$^1$H NMR (400 MHz, $CDCl_3$) δ2.00 (s, 3H), 2.02 (s, 3H), 2.03 (s, 3H), 2.08 (s, 3H), 2.46 (s, 3H), 3.58-3.60 (m, 2H), 3.65-3.72 (m, 4H), 3.89 (dt, $J_1$=11.7 Hz, $J_2$=4.1 Hz, 1H), 4.11-4.16 (m, 3H), 4.26 (dd, $J_1$=12.4 Hz, $J_2$=3.9 Hz, 1H), 4.58 (d, J=8.3 Hz, 1H), 4.98 (t, J=8.8 Hz, 1H), 5.08 (t, J=9.5 Hz, 1H), 5.21 (t, J=9.5 Hz, 1H).

—Synthesis of Compound (II)—

To p-nitrophenol (182 mg, 1.29 mmol) and $K_2CO_3$ (413 mg, 2.98 mmol), N,N-dimethyl formamide (DMF) (10.0 mL) was added under argon atmosphere. To this, the compound (10) (587 mg, 0.99 mmol) dissolved in DMF (9.5 mL) was added, and the resulting mixture was stirred at 100° C. for 4 hours. $K_2CO_3$ was removed with suction filtration from the obtained solution, and then water was added and the resulting mixture was extracted with $CH_2Cl_2$. The organic layer was washed with saturated saline, and dried with $Na_2SO_4$. The obtained reaction mixture was purified with silica gel column chromatography (ethyl acetate/hexane=1:1), to give the targeted compound, that is, the compound (II) as a yellow syrup-like liquid (81% yield rate, 446 mg yield amount).

The NMR measurement result of the compound (II) was as described below.

$^1$H NMR (400 MHz, CDCl3) δ2.01 (s, 3H), 2.02 (s, 3H), 2.08 (s, 3H), 3.66-3.78 (m, 4H), 3.87 (t, J=4.6 Hz, 2H), 3.96-4.00 (m, 1H), 4.14 (dd, $J_1$=12.2 Hz, $J_2$=2.4 Hz, 1H), 4.20 (t, J=4.9 Hz, 2H), 4.25 (dd, $J_1$=12.7 Hz, $J_2$=8.3 Hz, 1H), 4.59 (d, J=7.8 Hz, 1H), 5.00 (t, J=8.3 Hz, 1H), 5.08 (t, J=10.0 Hz, 1H), 5.19 (t, J=9.0 Hz, 1H), 6.99 (d, J=8.3 Hz, 2H), 8.21 (d, J=8.3 Hz, 2H).

—Synthesis of Compound (12)—

To the compound (II) (446 mg, 0.80 mmol), ethyl acetate (AcOEt) (8.4 mL) was added under argon atmosphere, and further palladium carbon catalyst (Pd/C) (46 mg, 10% by weight) was added and the reaction solution was hydrogen-substituted for 18 hours. Pd/C was removed by natural filtration from the obtained solution, and the obtained reaction mixture was purified with silica gel column chromatography (ethyl acetate/hexane=1:1), to give the targeted compound, that is, the compound (12) as a yellow syrup-like liquid (55% yield rate, 232 mg yield amount).

The NMR measurement result of the compound (12) was as described below.

$^1$H NMR (400 MHz, CDCl$_3$) δ2.00 (s, 3H), 2.02 (s, 3H), 2.03 (s, 3H), 2.08 (s, 3H), 3.43 (s, 2H), 3.66-3.72 (m, 4H), 3.75-3.79 (m, 4H), 3.96 (dt, $J_d$=11.5 Hz, $J_t$=4.4 Hz, 1H), 4.03 (t, J=3.4 Hz, 2H), 4.13 (dd, $J_1$=12.2 Hz, $J_2$=2.4 Hz, 1H), 4.25 (dd, $J_1$=12.4 Hz, $J_2$=4.4 Hz, 1H), 4.61 (d, J=7.8 Hz, 1H), 4.99 (dd, $J_1$=9.5 Hz, $J_2$=8.3 Hz, 1H), 5.08 (t, J=9.8 Hz, 1H), 5.20 (t, J=9.8 Hz, 1H), 6.63 (d, J=8.8 Hz, 2H), 6.77 (d, J=8.8 Hz, 2H).

—Synthesis of Compound (13)—

To the compound (12) (375 mg, 0.71 mmol), 1,2-dichloroethane (1.5 mL) was added under argon atmosphere. To this, triphosgene (218 mg, 0.74 mmol) dissolved in 1,2-dichloroethane (1.4 mL) was added. To the obtained solution, triethyl amine (Et$_3$N) (0.22 mL, 1.56 mmol) was added under ice cooling, and the reaction solution was stirred at room temperature for 40 minutes. The reaction solvent was distilled off from the solution after the stirring, and then 1,2-dichloroethane (2.9 mL) was added, and further the unpurified compound (7) (40 mg, 0.24 mmol) was added. The obtained solution was stirred at 90° C. for 2 days, and then quenched with a saturated aqueous solution of ammonium chloride, and extracted with CH$_2$Cl$_2$. The organic layer was washed with saturated saline, and dried with Na$_2$SO$_4$. The obtained reaction mixture was purified with silica gel column chromatography (acetone/CH$_2$Cl$_2$=1:3→1:0), to give the targeted compound, that is, the compound (13) as an ocher solid (78% yield rate, 347 mg yield amount).

The NMR measurement result of the compound (13) was as described below.

$^1$H NMR (400 MHz, DMSO-d$_6$) δ1.93 (s, 9H), 1.98 (d, J=1.0 Hz, 18.0 Hz), 2.01 (s, 9H), 3.53-3.58 (m, 6H), 3.62-3.70 (m, 9H), 3.82 (dt, J=11.2 Hz, 4.3 Hz, 3H), 3.95-4.00 (m, 12H), 4.17 (dd, $J_1$=11.7 Hz, $J_2$=4.9 Hz, 3H), 4.25 (d, J=5.9 Hz, 6H), 4.76 (t, J=9.0 Hz, 3H), 4.84 (d, J=7.8 Hz, 3H), 4.90 (t, J=9.8 Hz, 3H), 5.26 (t, J=9.5 Hz, 3H), 6.52 (t, J=5.6 Hz, 3H), 6.79 (d, J=8.8 Hz, 6H), 7.10 (s, 3H), 7.28 (d, J=8.8 Hz, 6H), 8.35 (s, 3H).

—Synthesis of Exemplary Compound (I-2)—

To the compound (13) (73 mg, 0.040 mmol), ethanol (EtOH) (1.5 mL) was added under argon atmosphere. To the obtained solution, sodium ethoxide (NaOEt) (8.5 mg, 0.13 mmol) was added, and the reaction solution was stirred at room temperature for 21 hours. The reaction solution after the stirring was dialyzed using a semipermeable membrane in water, and concentrated, to give the targeted compound, that is, the exemplary compound (I-2) as an ocher solid (76% yield rate, 40 mg yield amount).

The molecular weight of the exemplary compound (I-2) is 1321.

The NMR measurement result of the exemplary compound (I-2) was as described below.

$^1$H NMR (400 MHz, DMSO-d$_6$) δ2.92-2.99 (m, 3H), 3.00-3.17 (m, 12H), 3.40-3.44 (m, 3H), 3.59-3.73 (m, 18H), 3.89 (t, J=6.8 Hz, 3H), 3.99 (d, J=4.4 Hz, 6H), 4.15 (d, J=7.8 Hz, 3H), 4.25 (d, J=4.9 Hz, 6H), 4.51 (t, J=5.6 Hz, 3H), 4.93 (dd, $J_1$=16.6 Hz, $J_2$=4.4 Hz, 6H), 5.01 (d, J=4.4 Hz, 3H), 6.53 (s, 3H), 6.80 (d, J=8.8 Hz, 6H), 7.10 (s, 3H), 7.28 (d, J=8.8 Hz, 6H), 8.36 (s, 3H).

<Synthesis of Exemplary Compound (I-21)>

The exemplary compound (I-21) was synthesized according to the synthesis route described below.

In the synthesis route described below, "TBS" represents a t-butyldimethyl silyl group.

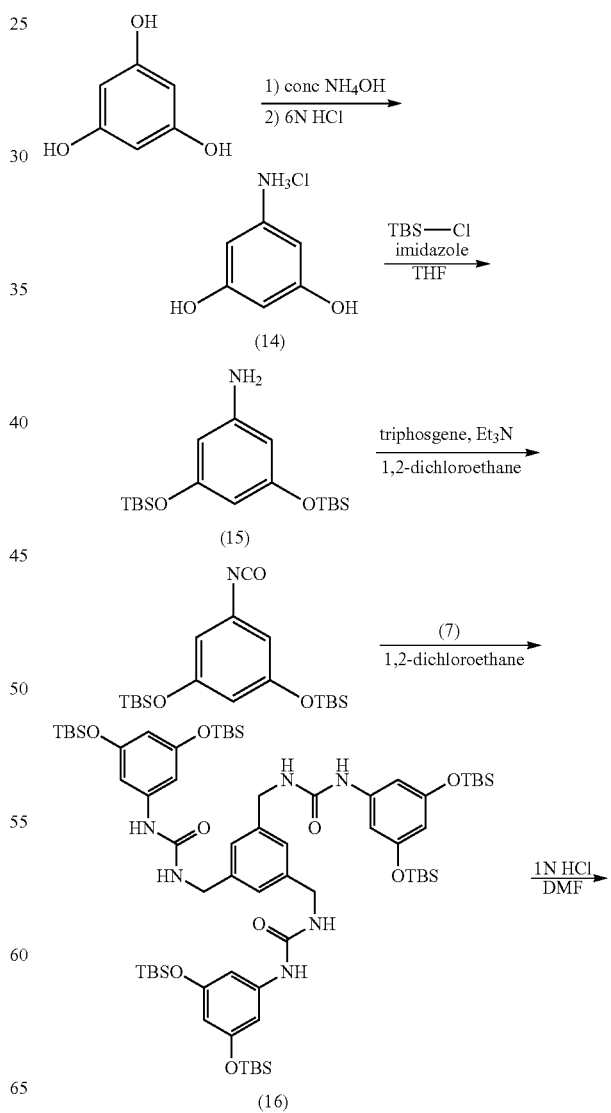

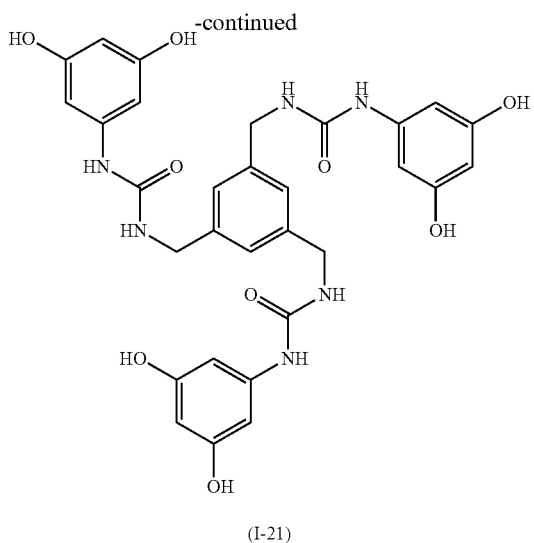

(I-21)

Hereinafter, specific manipulations of the synthesis route will be explained.

—Synthesis of Compound (14)—

To phloroglucinol (10.0 g, 79.5 mmol), conc. ammonia water (conc.NH$_4$OH) (78 mL) was added under argon atmosphere. The obtained solution was stirred at room temperature for one day, and then the solvent was distilled off under reduced pressure. To the obtained solution, 6N HCl was added under ice cooling to form a hydrochloric acid salt, and the solvent was distilled off under reduced pressure, and then the resultant was purified with MeOH/CH$_2$Cl$_2$ reprecipitation, to give the targeted compound, that is, the compound (14) as a yellow solid (69% yield rate, 8.89 g yield amount).

The NMR measurement result of the compound (14) was as described below.

$^1$H NMR (400 MHz, CD$_3$OD) δ6.27 (s, 2H), 6.32 (s, 1H).

—Synthesis of Compound (15)—

To the compound (14) (542 mg, 3.34 mmol) and imidazole (1.01 g, 14.8 mmol), THF (20.0 mL) was added under argon atmosphere. To the obtained solution, t-butyldimethyl silyl chloride (TBS-Cl) (2.02 g, 13.4 mmol) dissolved in THF (13.6 mL) was added with transfer under ice cooling, and then the resulting mixture was stirred at room temperature for 37 hours. The organic layer was sequentially washed with H$_2$O and saturated saline, dried with addition of Na$_2$SO$_4$, subjected to natural filtration, and further concentrated. The obtained reaction mixture was purified with silica gel column chromatography (ethyl acetate/hexane=1:50), to give the targeted compound, that is, the compound (15) as a white solid (72% yield rate, 937 mg yield amount).

The NMR measurement result of the compound (15) was as described below.

$^1$H NMR (600 MHz, CDCl$_3$) δ0.18 (s, 12H), 0.96 (s, 18H), 3.54 (s, 2H), 5.78 (t, J=2.0 Hz, 1H), 5.84 (d, J=2.0 Hz, 2H).

—Synthesis of Compound (16)—

To the compound (15) (599 mg, 1.53 mmol), 1,2-dichloroethane (2.5 mL) was added under argon atmosphere. To the obtained solution, triphosgene (456 mg, 1.54 mmol) dissolved in 1,2-dichloroethane (2.7 mL) was added, and subsequently triethyl amine (Et$_3$N) (0.44 mL, 3.07 mmol) was added under ice cooling, and the reaction solution was stirred at room temperature for 1 hour. The solvent was distilled off under reduced pressure from the solution after the stirring to give a white the solid. Then, 1,2-dichloroethane (5.2 mL) was added, and the unpurified compound (7) (76 mg, 0.46 mmol) was further added, and the resulting mixture was stirred at 50° C. for 2.5 days. The reaction was quenched with a saturated aqueous solution of ammonium chloride, and extraction with CHCl$_3$ was performed. The obtained organic layer was washed with H$_2$O and saturated saline. The organic layer was dried with addition of Na$_2$SO$_4$, subjected to natural filtration, and further concentrated. The obtained reaction mixture was purified with silica gel column chromatography (CHCl$_3$/ethyl acetate=50:1), to give the targeted compound, that is, the compound (16) as an ocher solid (64% yield rate, 385 mg yield amount).

The NMR measurement result of the compound (16) was as described below.

$^1$H NMR (600 MHz, DMSO-d$_6$) δ0.15 (s, 36H), 0.92 (s, 54H), 4.26 (d, J=5.5 Hz, 6H), 5.83 (s, 3H), 6.52 (t, J=5.8 Hz, 3H), 6.62 (d, J=2.1 Hz, 6H), 7.11 (s, 3H), 8.53 (s, 3H).

—Synthesis of Exemplary Compound (I-21)—

To the compound (16) (107 mg, 0.082 mmol), DMF (7.0 mL) was added under argon atmosphere. 1N HCl (1.3 mL) was dropped under ice cooling, and then and the resulting mixture was stirred at room temperature for 5 days. The reaction was quenched with addition of a saturated aqueous solution of sodium hydrogen carbonate, and the solvent was distilled off under reduced pressure. The obtained solid was purified with MeOH/H$_2$O reprecipitation, to give the targeted compound, that is, the exemplary compound (I-21) as an ocher solid (37% yield rate, 19 mg yield amount).

The molecular weight of the exemplary compound (I-21) is 618.

The NMR measurement result of exemplary compound (I-21) was as described below.

$^1$H NMR (600 MHz, DMSO-d$_6$) δ4.24 (d, J=5.5 Hz, 6H), 5.76 (t, J=2.1 Hz, 3H), 6.35 (d, J=2.1 Hz, 6H), 6.45 (t, J=5.8 Hz, 3H), 7.09 (s, 3H), 8.29 (d, J=26.8 Hz, 3H), 9.01 (s, 6H).

Although the synthesis examples of the exemplary compounds (1-2) and (1-21) have been explained above, other compounds represented by general formula (I) can be also synthesized in a similar method to these synthesis examples by reacting the compound (7) (1,3,5-Tris(amino methyl)benzene) with an aromatic compound having a hydrophilic group protected with a protective group, and an isocyanate group (—NCO group), and then performing the deprotection.

Example 2

<<Gelation of Aqueous Sample with Exemplary Compound (I-2)>>

Using the exemplary compound (I-2) synthesized above as a gelation agent, gelation of various aqueous samples described below was performed.

<Aqueous Sample>

Water

Tris-glycine-sodium dodecyl sulfate buffer (hereinafter, also referred to as the "Tris-Glycine-SDS buffer")

Dulbecco's Modified Eagle's Medium (hereinafter, also referred to as the "D-MEM")

Tris-hydrochloric acid buffer (hereinafter, also referred to as the "Tris-HCl buffer")

Borate-sodium hydroxide buffer (hereinafter, also referred to as the "Borate NaOH buffer")

Tris-borate-ethylene diamine tetraacetic acid buffer (hereinafter, also referred to as the "Tris-Borate-EDTA buffer")

Aqueous solution of hydrochloric acid

Aqueous solution of sodium hydroxide

Saline 4-(2-hydroxyethyl)-1-piperazineethane sulfonic acid-sodium hydroxide buffer (hereinafter, also referred to as the "HEPES-NaOH buffer")

Phosphate buffered saline (hereinafter, also referred to as the "PBS buffer")

Glycine-sodium hydroxide buffer (hereinafter, also referred to as the "Glycine-NaOH buffer")

Glycine-hydrochloric acid buffer (hereinafter, also referred to as the "Glycine-HCl buffer")

Phosphate buffer (hereinafter, also referred to as the "Phosphate buffer")

Sodium dihydrogen phosphate-sodium hydroxide buffer (hereinafter, also referred to as the "NaH$_2$PO$_4$—NaOH buffer")

Aqueous solution of any of various inorganic salts (NaF, NaCl, NaBr, NaOAc, Na$_2$CO$_3$, Na$_2$SO$_3$, Na$_2$SO$_4$, Na$_3$PO$_4$, NH$_4$F, NH$_4$C$_1$, NH$_4$Br)

Sea water

<Manipulation of Gelation>

To a microtube (2.2 mL volume, 5 mm inner diameter), the gelation agent and the aqueous sample (100 μL) were added, and the microtube was heated (about 100° C.) to dissolve the gelation agent, and then allowed to cool at room temperature for 2 hours.

<Evaluation of Gelation>

With respect to each sample after the cooling, evaluation of the gelation was performed according to the evaluation criteria described below.

—Evaluation Criteria—

G (gel) . . . A case where when the microtube is tuned upside down with the bottom up and the opening down, the aqueous sample does not flow downward after lapse of 60 seconds, and, even when the microtube is tilted, the gel does not flow.

PG (partial gel) . . . A case where the gel is partially formed.

I (insoluble) . . . A case where the gelation agent is hardly dissolved in the solvent.

V (viscous solution) . . . A case where the aqueous sample is viscous while when the microtube is tuned upside down with the bottom up and the opening down, the aqueous sample flows downward within 60 seconds.

S (solution) . . . A case where the aqueous sample is not viscous while when the microtube is tuned upside down with the bottom up and the opening down, the aqueous sample flows downward within 60 seconds.

<Transparency>

With respect to each sample after the cooling, the transparency of the gel was determined according to the criteria described below.

With progress of the gelation, the transparency of the gel tends to decrease.

—Criteria—

A: A case where the gel is colorless and transparent.

B: A case where a letter is readable through the gel.

C: A case where a letter is barely recognized through the gel.

D: A case where a letter is not readable through the gel.

<Evaluation Results for Water>

The evaluation results when water was used as the aqueous sample are described in Table 1 and FIG. 1 described below.

The section of the concentration in Table 1 represents the concentration of the gelation agent in each sample (this is the same in the following tables).

Figure 2:
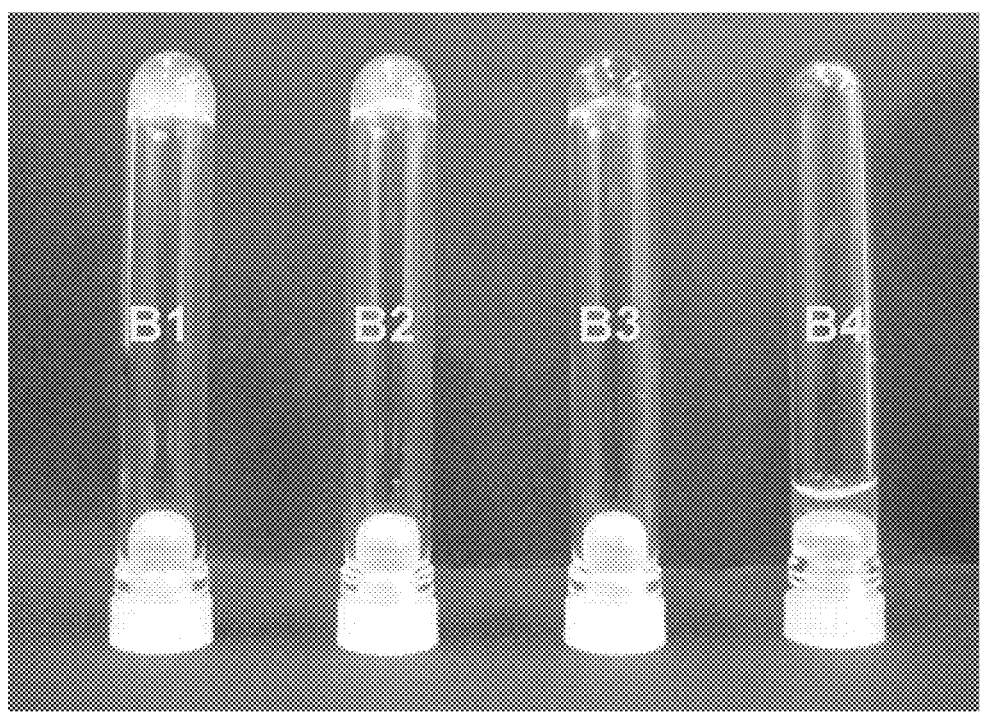
FIG. 2 is a photograph showing gelations of Tris-Glycine-SDS buffer were performed in Example 2.
Figure 3:
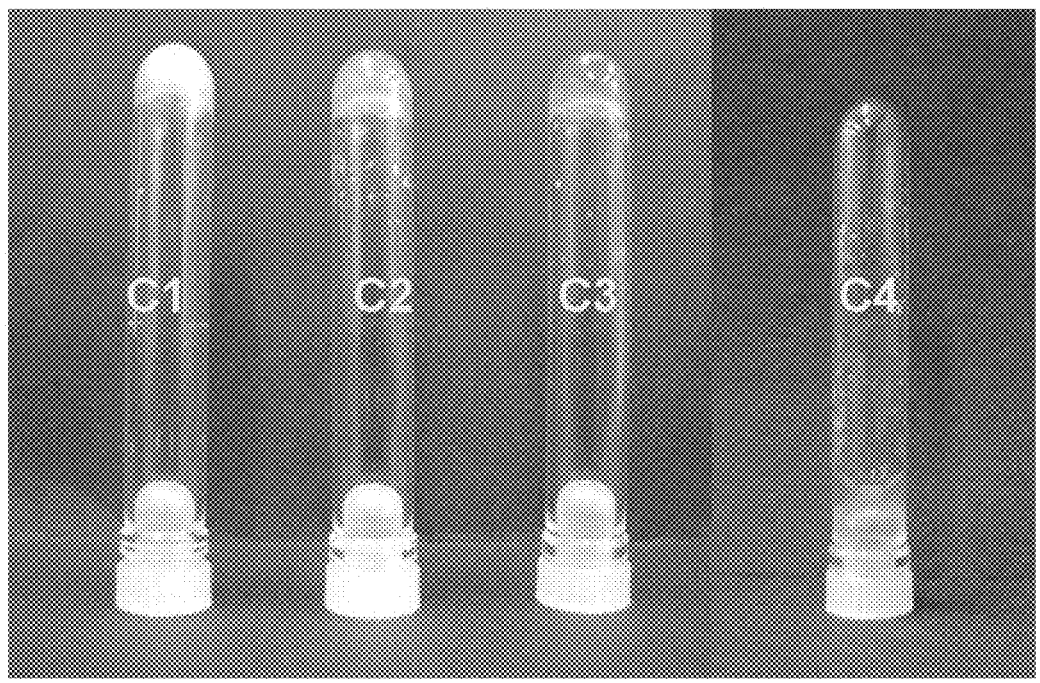
FIG. 3 is a photograph showing gelations of D-MEM were performed in Example 2.

FIG. 1 is a photograph of microtubes where the microtubes are turned upside down with the bottom up and the opening down after the manipulation of the gelation, and the symbol such as "A1" attached to the microtube represents the sample number (this is the same in the FIGS. 2 and 3).

TABLE 1

| Sample No. | Concentration (% by mass) | Evaluation | Transparency |
|---|---|---|---|
| A1 | 2.0 | G | D |
| A2 | 1.5 | G | D |
| A3 | 1.0 | G | C |
| A4 | 0.50 | G | B |
| A5 | 0.25 | S | A |

As described in Table 1 and FIG. 1, it was possible to perform gelation of water by adding the exemplary compound (I-2).

The minimum concentration for gelation was 0.50% by mass.

<Thermal Stability of Gel>

The gels of the sample numbers A1 to A3 maintained the state of the gel when heated to at least 90° C., which confirmed that the gels had high thermal stability.

Specifically, the temperatures where the gels of the sample numbers A1 to A3 changed to sol (hereinafter, referred to as "$T_{gel}$") were 96.9° C. (the sample number A1), 96.5° C. (sample number A2) and 95.9° C. (sample number A3), respectively.

<Temporal Stability of Gel>

The gel of the sample number A3 was left under the atmosphere (room temperature), and the gel maintained the gel state for least 5 months under the atmosphere. When the gel of the sample number A3 was left in water (room temperature), the gel maintained the gel state in water for at least 3 months.

From the results described above, it was confirmed that the obtained gel had high temporal stability.

(Comparative Experiment)

Next, as a comparative experiment, the manipulations were performed similarly to those of the evaluations for water except that the exemplary compound (I-2) was changed to the exemplary compound (3) described in the pamphlet of WO2010/101147, and the minimum concentration for the gelation of the exemplary compound (3) was obtained.

The minimum concentration for the gelation in the case where the exemplary compound (3) described in the pamphlet was used was 1.5% by mass.

By this, it was found out that the compound represented by general formula (I) of the present invention in which the central benzene ring and each of the three urea structures are bonded with a methylene group (—CH$_2$— group) has prominently superior gelation performance.

Meanwhile, the exemplary compound (3) described in the pamphlet is the same as the structure of the exemplary compound (I-2) except that the central benzene ring and each of the three urea structures are bonded via the divalent group of the structure described below (* represents the bonding site with the benzene ring, and ** represents the bonding site with the nitrogen atom of the urea structure).

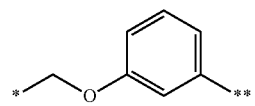

<Evaluation Results for Tris-Glycine-SDS Buffer>

The evaluation results when a Tris-Glycine-SDS buffer was used as the aqueous sample are described in Table 2 and FIG. 2 described below.

As the Tris-Glycine-SDS buffer, a Tris (25 mM)-Glycine (192 mM)-SDS (0.1%) buffer was used.

TABLE 2

| Sample No. | Concentration (% by mass) | Evaluation | Transparency |
|---|---|---|---|
| B1 | 3.0 | G | D |
| B2 | 2.0 | G | C |
| B3 | 1.5 | G | B |
| B4 | 1.0 | V | A |

As described in Table 2 and FIG. 2, it was possible to perform gelation of the Tris-Glycine-SDS buffer by adding the exemplary compound (I-2).

The minimum concentration for the gelation was 1.5% by mass.

<Evaluation Results for D-MEM>

The evaluation results when D-MEM was used as the aqueous sample are described in Table 3 and FIG. 3 described below.

TABLE 3

| Sample No. | Concentration (% by mass) | Evaluation | Transparency |
|---|---|---|---|
| C1 | 2.0 | G | D |
| C2 | 0.75 | G | D |
| C3 | 0.60 | G | C |
| C4 | 0.50 | S | B |

As described in Table 3 and FIG. 3, it was possible to perform gelation of the D-MEM by adding the exemplary compound (I-2).

The minimum concentration for the gelation was 0.60% by mass.

Separately, a gel of the D-MEM sample containing 1.0% by mass of the concentration of the gelation agent was prepared, and $T_{gel}$ of this gel was measured. As a result thereof, $T_{gel}$ was 103.7° C., which confirmed that this gel had high thermal stability.

<Evaluation Results for Tris-HCl Buffer (pH 7.4)>

The evaluation results when Tris-HCl buffer was used as the aqueous sample are listed in Table 4 described below.

Meanwhile, a drawing (photograph of the gel) with respect to the evaluation results of Table 4 or the following tables will be skipped.

TABLE 4

| Sample No. | Concentration (% by mass) | Evaluation | Transparency |
|---|---|---|---|
| D1 | 1.0 | G | D |
| D2 | 0.75 | G | D |
| D3 | 0.50 | G | D |

As shown in Table 4, it was possible to perform gelation of the Tris-HCl buffer by adding the exemplary compound (I-2).

The minimum concentration for the gelation was 0.50% by mass or less.

<Evaluation Results for Borate NaOH Buffer>

(Borate NaOH buffer (50 mM, pH 7.0))

The evaluation results when a Borate NaOH buffer (50 mM, pH 7.0) was used as the aqueous sample are listed in Table 5 described below.

TABLE 5

| Sample No. | Concentration (% by mass) | Evaluation | Transparency |
|---|---|---|---|
| E1 | 2.0 | G | D |
| E2 | 1.5 | G | D |
| E3 | 1.0 | G | D |
| E4 | 0.50 | G | C |
| E5 | 0.25 | V | B |

As shown in Table 5, it was possible to perform gelation of the Borate NaOH buffer (50 mM, pH 7.0) by adding the exemplary compound (I-2).

The minimum concentration for the gelation was 0.50% by mass.

In addition, $T_{gel}$ of the gel of sample number E3 was 96.4° C., which confirmed that this gel had high thermal stability.

(Borate NaOH buffer (pH 8.5))

The evaluation results when the concentration of Borate NaOH in a Borate NaOH buffer (pH 8.5) was changed are listed in Table 6 described below. The "concentration (mM)" section in Table 6 is the concentration of Borate NaOH. Herein, the concentration of the gelation agent was 0.5% by mass for any sample.

TABLE 6

| Sample No. | Concentration (% by mass) | Evaluation | Transparency |
|---|---|---|---|
| F1 | 200 | G | A |
| F2 | 100 | G | A |
| F3 | 50 | G | A |
| F4 | 25 | G | B |

As shown in Table 6, it was possible to perform gelation of various concentrations of Borate NaOH buffer (pH 8.5) by adding the exemplary compound (I-2).

<Evaluation Results for Tris-Borate-EDTA Buffer>

The evaluation results when a Tris-Borate-EDTA buffer was used as the aqueous sample are listed in Table 7 described below.

TABLE 7

| Sample No. | Concentration (% by mass) | Evaluation | Transparency |
|---|---|---|---|
| G1 | 2.0 | G | C |
| G2 | 0.50 | G | B |
| G3 | 0.25 | V | A |

As shown in Table 7, it was possible to perform gelation of the Tris-Borate-EDTA buffer by adding the exemplary compound (I-2).

The minimum concentration for the gelation was 0.50% by mass.

<pH Responsivity 1>

Gelations of aqueous samples of various pHs (an aqueous solution of hydrochloric acid (HCl aq.), water (H$_2$O), an aqueous solution of sodium hydroxide (NaOH aq.)) as the aqueous sample were performed, and the pH responsivity of the gelation performance was investigated.

The concentration of the gelation agent was 1.0% by mass for any sample.

The evaluation results are listed in Table 8 described below.

TABLE 8

| Sample No. | Aqueous sample | pH | Evaluation | Transparency |
|---|---|---|---|---|
| H1 | HCl aq, | 1.0 | G | D |
| H2 | HCl aq, | 2.0 | G | D |
| H3 | HCl aq, | 3.0 | G | D |
| H4 | HCl aq, | 4.0 | G | D |
| H5 | HCl aq, | 5.0 | G | D |
| H6 | HCl aq, | 6.0 | G | D |
| H7 | $H_2O$ | 7.0 | G | D |
| H8 | NaOH aq. | 8.0 | G | D |
| H9 | NaOH aq. | 9.0 | G | D |
| H10 | NaOH aq. | 10.0 | G | D |
| H11 | NaOH aq. | 11.0 | G | D |
| H12 | NaOH aq. | 12.0 | G | D |

As shown in Table 8, it was possible to perform gelation of an aqueous sample in a range of pH 1.0 to 12.0 by adding the exemplary compound (I-2).

In addition, $T_{gel}$ of the gel of each of the sample numbers H1 to H12 was 95° C. or higher for any sample, which confirmed that these gels had high thermal stability.

(Comparative Experiment)

Next, as a comparative experiment, evaluation was performed similarly to those of the pH responsivity evaluations except that the exemplary compound (I-2) was changed to the exemplary compound (3) described in the pamphlet of WO2010/101147.

Then, the pH where the gelation was performed for the exemplary compound (3) was in a range of about 6.0 to 9.0.

From this result, it was found out that the compound represented by general formula (I) of the present invention of the structure in which the central benzene ring and each of the three urea structures are bonded with a methylene group (—$CH_2$— group) allows gelation of an aqueous sample in a wide range of pH.

<pH Responsivity 2>

Evaluation was performed similarly to those of the pH responsivity 1 except that the pH of a Borate NaOH buffer (50 mM) as the aqueous sample was changed to various values.

The concentration of the gelation agent was 0.50% by mass for any sample.

The evaluation results are listed in Table 9 described below.

TABLE 9

| Sample No. | pH | Evaluation | Transparency |
|---|---|---|---|
| 11 | 6.3 | G | D |
| 12 | 6.5 | G | D |
| 13 | 7.0 | G | C |
| 14 | 8.0 | G | B |
| 15 | 8.5 | G | A |
| 16 | 9.0 | G | A |

As shown in Table 9, it was possible to perform gelation of the Borate NaOH buffer (50 mM) of various pHs by adding the exemplary compound (I-2).

<Evaluation Results for Saline>

The evaluation results when various salt concentrations of saline were used as the aqueous sample are listed in Table 10 described below.

The concentration of the gelation agent was 1.0% by mass for any sample.

TABLE 10

| Sample No. | Concentration of salt | Evaluation | Transparency |
|---|---|---|---|
| J1 | 9.0% | G | D |
| J2 | 0.90% (Physiological saline) | G | D |

As shown in Table 10, it was possible to perform gelation of the saline by adding the exemplary compound (I-2).

In addition, $T_{gel}$ of the gel of the sample number J2 was 99.6° C., which confirmed that this gel had high thermal stability.

<Evaluation Results for HEPES-NaOH Buffer>

The evaluation results when a HEPES-NaOH buffer (pH 7.5) was used as the aqueous sample are listed in Table 11 described below. The concentration of the gelation agent was 1.0% by mass.

TABLE 11

| Sample No. | Aqueous sample | Concentration (% by mass) | Evaluation | Transparency |
|---|---|---|---|---|
| K1 | HEPES-NaOH Buffer (ph 7.5) | 1.0 | G | D |

As shown in Table 11, it was possible to perform gelation of the HEPES-NaOH buffer (pH 7.5) by adding the exemplary compound (I-2).

<pH Responsivity of HEPES-NaOH Buffer>

Evaluation was performed similarly to those of the evaluations of the HEPES-NaOH buffer (pH 7.5) except that the pH of the HEPES-NaOH buffer (pH 7.5) was changed to various values as listed in Table 12 described below (the concentration of the gelation agent was 1.0% by mass for any sample). The evaluation results are listed in Table 12 described below.

TABLE 12

| Sample No. | Aqueous sample | pH | Evaluation |
|---|---|---|---|
| K2 | HEPES + NaOH Buffer | 5.3 | G |
| K3 | HEPES + NaOH Buffer | 6.0 | G |
| K4 | HEPES + NaOH Buffer | 7.0 | G |
| K5 | HEPES + NaOH Buffer | 8.0 | G |
| K6 | HEPES + NaOH Buffer | 9.0 | G |
| K7 | HEPES + NaOH Buffer | 10.0 | G |
| K8 | HEPES + NaOH Buffer | 11.0 | G |
| K9 | HEPES + NaOH Buffer | 12.0 | G |

As shown in Table 12, it was possible to perform gelation of the HEPES-NaOH buffer of various pHs by adding the exemplary compound (I-2).

In addition, $T_{gel}$ of the gel of the sample number K4 was 98.9° C., which confirmed that this gel had high thermal stability.

<Evaluation Results for Other Buffer>

The evaluation results when the buffers other than those described above were used as the aqueous sample, and the minimum concentration for the gelation are shown in Table 13 described below.

TABLE 13

| Buffer | Minimum concentration for gelation (% by mass) | Evaluation |
|---|---|---|
| PBS buffer | 1.0 | G |
| Glycine-NaOH buffer | 1.0 | G |

TABLE 13-continued

| Buffer | Minimum concentration for gelation (% by mass) | Evaluation |
| --- | --- | --- |
| Glycine-HCl buffer | 1.0 | G |
| Phosphate buffer | 1.0 | G |
| NaH$_2$PO$_4$—NaOH buffer | 1.0 | G |

As shown in Table 13, it was possible to perform gelation of the buffer by adding the exemplary compound (I-2).

In addition, T$_{gel}$ of the gel of the PBS buffer was 97.1° C., and T$_{gel}$ of the gel of the Glycine-NaOH buffer was 100.5° C., which confirmed that these gels had high thermal stability.

<Evaluation Results for Aqueous Solutions of Various Inorganic Salts>

The evaluation results when various aqueous solutions of inorganic salts including sea water as the aqueous sample were used are listed in Table 14 described below. The amount (eq.) of the inorganic salt in Table 14 described below represents an equivalent with respect to the amount of the gelation agent, and "saturated" represents the saturation amount.

TABLE 14

| Aqueous solution of inorganic salt | | | |
| --- | --- | --- | --- |
| Inorganic salt | | Concentration of gelation agent | |
| Kind | Amount | (% by mass) | Evaluation |
| NaF | 400 eq. | 0.25 | G |
|  | 700 eq. | 0.25 | G |
|  | 700 eq. | 1.0 | G |
|  | 1000 eq. | 0.25 | G |
|  | 2000 eq. | 0.25 | G |
|  | saturated | 0.25 | G |
| NaCl | 400 eq. | 0.25 | G |
|  | 700 eq. | 0.25 | G |
|  | 700 eq. | 1.0 | G |
|  | 1000 eq. | 0.25 | G |
|  | 2000 eq. | 0.25 | G |
|  | saturated | 0.25 | G |
| NaBr | 400 eq. | 0.25 | G |
|  | 700 eq. | 0.25 | G |
|  | 700 eq. | 1.0 | G |
|  | 1000 eq. | 0.25 | G |
|  | 2000 eq. | 0.25 | G |
|  | saturated | 1.0 | G |
| NaOAc | 25 eq. | 1.0 | G |
|  | 50 eq. | 1.0 | G |
|  | 100 eq. | 1.0 | G |
|  | 200 eq. | 1.0 | G |
|  | saturated | 1.0 | G |
| Na$_2$CO$_3$ | 25 eq. | 1.0 | G |
|  | 50 eq. | 1.0 | G |
|  | 100 eq. | 1.0 | G |
|  | 200 eq. | 1.0 | G |
|  | saturated | 1.0 | G |
| Na$_2$SO$_3$ | 25 eq. | 1.0 | G |
|  | 50 eq. | 1.0 | G |
|  | 100 eq. | 1.0 | G |
|  | 200 eq. | 1.0 | G |
| Na$_2$SO$_4$ | saturated | 1.0 | G |
| Na$_3$PO$_4$ | saturated | 1.0 | G |
| NH$_4$F | saturated | 1.0 | G |
| NH$_4$Cl | saturated | 1.0 | G |
| NH$_4$Br | saturated | 1.0 | G |
| Sea water |  | 0.25 | G |

As shown in Table 14, it was possible to perform gelation of the various aqueous solutions of inorganic salts including sea water by adding the exemplary compound (I-2).

In addition, T$_{gel}$ of the gel of the saturated aqueous solution of NaCl was 121.1° C., and T$_{gel}$ of the gel of the saturated aqueous solution of NaF was 110.0° C., which confirmed that these gels had high thermal stability.

Example 3

<<Gelation of Aqueous Sample by Exemplary Compound (I-21)>>

Gelation of each of the aqueous samples of water, a Tris-HCl buffer (50 mM, pH 7.0) and a HEPES-NaOH buffer (50 mM, pH 7.0) was performed similarly to Example 2 except that the exemplary compound (I-2) was changed to the exemplary compound (I-21), and the minimum concentration for the gelation was measured.

The measurement results for the minimum concentration for the gelation are listed in Table 15 described below.

TABLE 15

| Aqueous sample | Aqueous sample |
| --- | --- |
| Water | 1.0% by mass |
| Tris-HCl Buffer (50 mM, pH7.0) | 1.5% by mass |
| HEPES-NaOH Buffer (50 mM, pH7.0) | 1.0% by mass |

As shown in Table 15, it was possible to perform gelation of each of the aqueous samples of water, the Tris-HCl buffer (50 mM, pH 7.0) and the HEPES-NaOH buffer (50 mM, pH 7.0) by adding small addition amount of the exemplary compound (I-21).

The disclosure of Japanese Patent application No. 2011-053564 is incorporated herein by reference in its entirety.

All publications, patent applications, and technical standards mentioned in this specification are herein incorporated by reference to the same extent as if such individual publication, patent application, or technical standard was specifically and individually indicated to be incorporated by reference.

The invention claimed is:

1. A substituted aromatic compound represented by the following general formula (I):

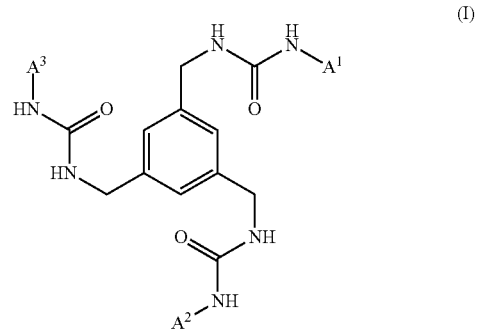

wherein in general formula (I), A$^1$, A$^2$, and A$^3$ each independently represent an aryl group substituted by a hydrophilic group.

2. The substituted aromatic compound according to claim 1, wherein the hydrophilic group comprises at least one selected from the group consisting of a —OH group, a —SO$_3$H group, a —SO$_3$M group, a —COOH group, a —COOM group, a —NR$^1$R$^2$R$^3$X group, a —NH$_2$ group, an alkyleneoxy group, and a saccharide group; M represents an alkali metal element; R$^1$, R$^2$, and R$^3$ each independently represent an alkyl group; and X represents a halogen element.

3. The substituted aromatic compound according to claim 1, wherein the hydrophilic group is at least one selected from the group consisting of a —OH group, a —SO$_3$H group, a —SO$_3$M group, a —COOH group, a —COOM group, a —NR$^1$R$^2$R$^3$X group, a —NH$_2$ group, and a group including an alkyleneoxy group and a saccharide group; M represents an alkali metal element; R$^1$, R$^2$, and R$^3$ each independently represent an alkyl group; and X represents a halogen element.

4. The substituted aromatic compound according to claim 1, wherein the hydrophilic group is at least one selected from the group consisting of a —OH group, and a —[(OE)$_n$S$_g$] group; E represents an ethylene group; n represents an integer from 1 to 4; and S$_g$ represents a saccharide group.

5. A hydrogelation agent, comprising the substituted aromatic compound according to claim 1.

6. A hydrogel, comprising the substituted aromatic compound according to claim 1.

7. A method for gelating an aqueous sample, the method comprising contacting the substituted aromatic compound according to claim 1 with the aqueous sample.

8. The hydrogelation agent according to claim 5, wherein the hydrophilic group comprises at least one selected from the group consisting of a —OH group, a —SO$_3$H group, a —SO$_3$M group, a —COOH group, a —COOM group, a —NR$^1$R$^2$R$^3$X group, a —NH$_2$ group, an alkyleneoxy group, and a saccharide group; M represents an alkali metal element; R$^1$, R$^2$, and R$^3$ each independently represent an alkyl group; and X represents a halogen element.

9. The hydrogelation agent according to claim 5, wherein the hydrophilic group is at least one selected from the group consisting of a —OH group, a —SO$_3$H group, a —SO$_3$M group, a —COOH group, a —COOM group, a —NR$^1$R$^2$R$^3$X group, a —NH$_2$ group, and a group including an alkyleneoxy group and a saccharide group; M represents an alkali metal element; R$^1$, R$^2$, and R$^3$ each independently represent an alkyl group; and X represents a halogen element.

10. The hydrogelation agent according to claim 5, wherein the hydrophilic group is at least one selected from the group consisting of a —OH group, and a —[(OE)$_n$S$_g$] group; E represents an ethylene group; n represents an integer from 1 to 4; and S$_g$ represents a saccharide group.

11. The hydrogel according to claim 6, wherein the hydrophilic group comprises at least one selected from the group consisting of a —OH group, a —SO$_3$H group, a —SO$_3$M group, a —COOH group, a —COOM group, a —NR$^1$R$^2$R$^3$X group, a —NH$_2$ group, an alkyleneoxy group, and a saccharide group; M represents an alkali metal element; R$^1$, R$^2$, and R$^3$ each independently represent an alkyl group; and X represents a halogen element.

12. The hydrogel according to claim 6, wherein the hydrophilic group is at least one selected from the group consisting of a —OH group, a —SO$_3$H group, a —SO$_3$M group, a —COOH group, a —COOM group, a —NR$^1$R$^2$R$^3$X group, a —NH$_2$ group, and a group including an alkyleneoxy group and a saccharide group; M represents an alkali metal element; R$^1$, R$^2$, and R$^3$ each independently represent an alkyl group; and X represents a halogen element.

13. The hydrogel according to claim 6, wherein the hydrophilic group is at least one selected from the group consisting of a —OH group, and a —[(OE)$_n$S$_g$] group; E represents an ethylene group; n represents an integer from 1 to 4; and S$_g$ represents a saccharide group.

14. The method for gelating an aqueous sample according to claim 7, wherein the hydrophilic group comprises at least one selected from the group consisting of a —OH group, a —SO$_3$H group, a —SO$_3$M group, a —COOH group, a —COOM group, a —NR$^1$R$^2$R$^3$X group, a —NH$_2$ group, an alkyleneoxy group, and a saccharide group; M represents an alkali metal element; R$^1$, R$^2$, and R$^3$ each independently represent an alkyl group; and X represents a halogen element.

15. The method for gelating an aqueous sample according to claim 7, wherein the hydrophilic group is at least one selected from the group consisting of a —OH group, a —SO$_3$H group, a —SO$_3$M group, a —COOH group, a —COOM group, a —NR$^1$R$^2$R$^3$X group, a —NH$_2$ group, and a group including an alkyleneoxy group and a saccharide group; M represents an alkali metal element; R$^1$, R$^2$, and R$^3$ each independently represent an alkyl group; and X represents a halogen element.

16. The method for gelating an aqueous sample according to claim 7, wherein the hydrophilic group is at least one selected from the group consisting of a —OH group, and a —[(OE)$_n$S$_g$] group; E represents an ethylene group; n represents an integer from 1 to 4; and S$_g$ represents a saccharide group.

* * * * *

UNITED STATES PATENT AND TRADEMARK OFFICE
CERTIFICATE OF CORRECTION

PATENT NO. : 9,115,164 B2  
APPLICATION NO. : 14/003907  
DATED : August 25, 2015  
INVENTOR(S) : Masamichi Yamanaka et al.

Page 1 of 1

It is certified that error appears in the above-identified patent and that said Letters Patent is hereby corrected as shown below:

On the Title Page:

At item (75), line 2, "Shizuaoka" should be -- Shizuoka --.

Signed and Sealed this  
Second Day of August, 2016

Michelle K. Lee  
*Director of the United States Patent and Trademark Office*